(12) United States Patent
Hammons et al.

(10) Patent No.: US 9,198,809 B2
(45) Date of Patent: *Dec. 1, 2015

(54) ABSORBENT ARTICLE COMPRISING FLUID HANDLING ZONES

(71) Applicant: The Procter & Gamble Company, Cincinnati, OH (US)

(72) Inventors: John Lee Hammons, Hamilton, OH (US); Ronald Bosman Visscher, Cincinnati, OH (US); Shreedhar Rajpanth Murthy, Cincinnati, OH (US); Jeffrey Tupper Roesgen, Anderson Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 151 days.

This patent is subject to a terminal disclaimer.

(21) Appl. No.: 14/022,274

(22) Filed: Sep. 10, 2013

(65) Prior Publication Data

US 2014/0031779 A1 Jan. 30, 2014

Related U.S. Application Data

(63) Continuation of application No. 13/024,369, filed on Feb. 10, 2011, now Pat. No. 8,569,572.

(51) Int. Cl.
*A61F 13/512* (2006.01)
*A61F 13/513* (2006.01)
*A61F 13/511* (2006.01)
*A61F 13/538* (2006.01)

(52) U.S. Cl.
CPC ............ *A61F 13/538* (2013.01); *A61F 13/512* (2013.01); *A61F 13/51305* (2013.01)

(58) Field of Classification Search
CPC ............ A61F 13/512; A61F 13/51305; A61F 13/5126; A61F 13/5128
See application file for complete search history.

(56) References Cited

U.S. PATENT DOCUMENTS

| | | | | |
|---|---|---|---|---|
| 5,658,639 A | * | 8/1997 | Curro et al. | 428/131 |
| 5,743,776 A | * | 4/1998 | Igaue et al. | 442/414 |
| 6,049,024 A | * | 4/2000 | Thomas et al. | 604/367 |
| 6,911,574 B1 | | 6/2005 | Mizutani | |

(Continued)

FOREIGN PATENT DOCUMENTS

| | | |
|---|---|---|
| EP | 1342459 B1 | 11/2005 |
| WO | WO-2007-069964 A1 | 6/2007 |

(Continued)

OTHER PUBLICATIONS

PCT International Search report dated May 2, 2011, 5 pages.

*Primary Examiner* — Susan Su
(74) *Attorney, Agent, or Firm* — George H. Leal; Andrew J. Hagerty

(57) ABSTRACT

An absorbent article comprising a topsheet, a backsheet, and an absorbent core disposed between the topsheet and the backsheet. The absorbent article comprises a first fluid handling zone having a first Transverse Fluid Travel Distance and a second fluid handling zone having a second Transverse Fluid Travel Distance. The first Transverse Fluid Travel Distance is at least about 50% greater than said second Transverse Fluid Travel Distance, which results in an absorbent article that is better able to handle bodily fluids and reduce the risk of accidental leakage of bodily fluids onto a consumer's undergarments.

16 Claims, 10 Drawing Sheets

(56) References Cited

U.S. PATENT DOCUMENTS

| | | | |
|---|---|---|---|
| 6,916,969 B1 | 7/2005 | Helmfridsson et al. | |
| 7,196,241 B2 | 3/2007 | Kinoshita et al. | |
| 7,589,249 B2 | 9/2009 | Gubernick et al. | |
| 2002/0028624 A1 | 3/2002 | Mizutani et al. | |
| 2003/0125687 A1* | 7/2003 | Gubernick et al. | 604/383 |
| 2004/0127875 A1 | 7/2004 | Hammons et al. | |
| 2004/0265534 A1* | 12/2004 | Curro et al. | 428/92 |
| 2005/0148971 A1 | 7/2005 | Kuroda et al. | |
| 2005/0154362 A1 | 7/2005 | Warren et al. | |
| 2008/0045915 A1 | 2/2008 | Noda et al. | |
| 2008/0294138 A1 | 11/2008 | Andersson et al. | |
| 2008/0300564 A1 | 12/2008 | Bogren et al. | |
| 2009/0030391 A1* | 1/2009 | Hammons et al. | 604/378 |
| 2009/0105678 A1 | 4/2009 | Minoguchi et al. | |
| 2009/0247978 A1 | 10/2009 | Boissier | |
| 2010/0004615 A1 | 1/2010 | Boissier | |
| 2010/0035014 A1 | 2/2010 | Hammons et al. | |
| 2010/0036338 A1 | 2/2010 | Hammons et al. | |
| 2010/0036349 A1 | 2/2010 | Hammons et al. | |
| 2011/0106036 A1 | 5/2011 | Ståhl et al. | |
| 2011/0313385 A1 | 12/2011 | Hammons et al. | |

FOREIGN PATENT DOCUMENTS

| | | |
|---|---|---|
| WO | WO-2007-116346 A1 | 10/2007 |
| WO | WO-2007-116347 A2 | 10/2007 |
| WO | WO-2010-017351 A1 | 2/2010 |

* cited by examiner

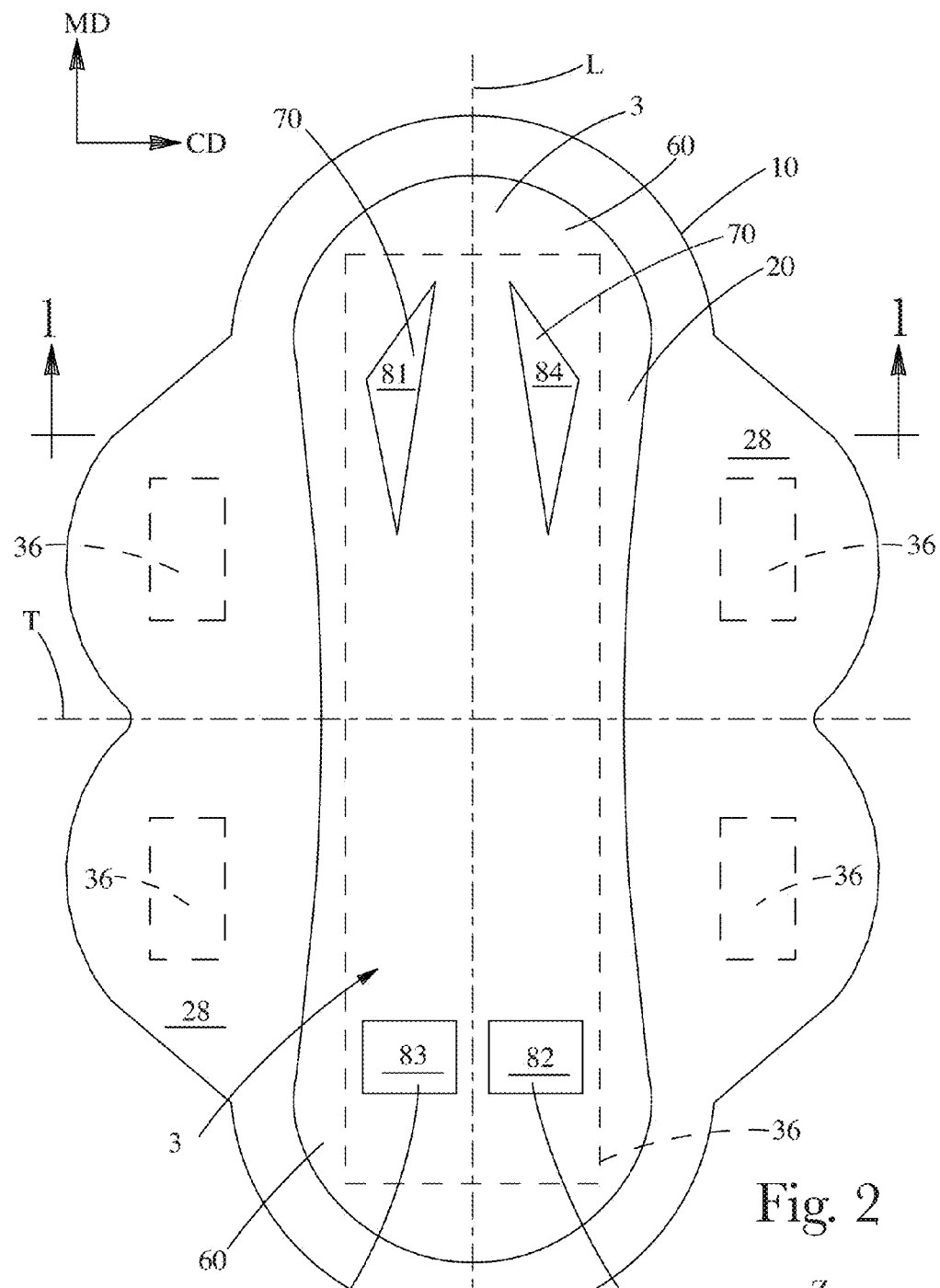
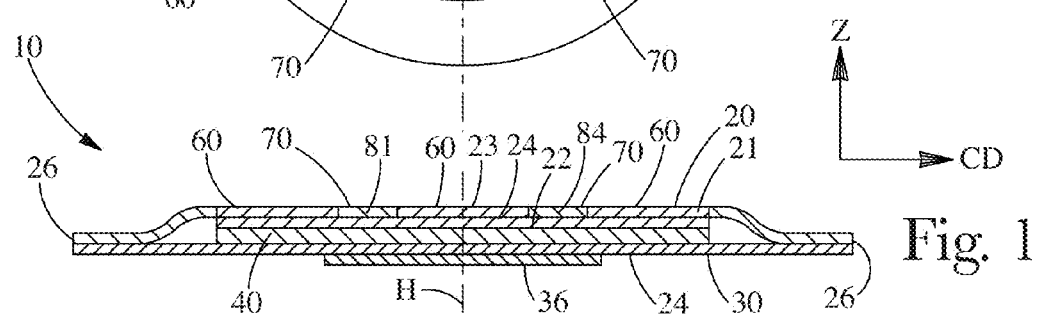
Fig. 2
Fig. 1

US 9,198,809 B2

ABSORBENT ARTICLE COMPRISING FLUID HANDLING ZONES

CROSS REFERENCE TO RELATED APPLICATION

This application is a continuation of application Ser. No. 13/024,369 filed Feb. 10, 2011, which claims the benefit of U.S. Provisional Application No. 61/303,657, filed Feb. 11, 2010.

FIELD OF THE INVENTION

The present invention relates to an absorbent article comprising a first fluid handling zone and a second fluid handling zone for improved handling of bodily fluids.

BACKGROUND OF THE INVENTION

Absorbent articles such as sanitary napkins, diapers, adult incontinence products, and the like are designed to be worn in close proximity to the crotch of the wearer to absorb bodily fluids such as menses.

A significant concern of consumers of absorbent articles such as sanitary napkins relates to the risk of leakage of bodily fluids. If an absorbent article cannot effectively absorb bodily fluids, there is a risk of the bodily fluid soiling the undergarments of the consumer. There are many conditions that can signal to a consumer as to whether an absorbent article is effectively absorbing bodily fluids such as menses. Absorbent articles that are better able to handle bodily fluids can result in absorbent articles that exhibit smaller stain sizes, less wetness, less runoff of bodily fluid, and smaller stains on the body from the bodily fluid.

With these limitations in mind, there remains a need for an absorbent article having a topsheet and/or absorbent core that provide different zones with different fluid handling properties so that bodily fluids can be more effectively contained by the absorbent article.

SUMMARY OF THE INVENTION

The present invention relates to an absorbent article comprising a topsheet, a backsheet, and an absorbent core disposed between the topsheet and the backsheet. The absorbent article comprises a first fluid handling zone comprising a first portion of said topsheet and having a first Transverse Fluid Travel Distance. The absorbent article further comprises a second fluid handling zone comprising a second portion of said topsheet and having a second Transverse Fluid Travel Distance. The first and second portions of the topsheet have different constructions. The first Transverse Fluid Travel Distance is at least about 50% greater than said second Transverse Fluid Travel Distance, which results in an absorbent article that is better able to handle bodily fluids and reduce the risk of accidental leakage of bodily fluids onto a consumer's undergarments.

The present invention further relates to a method of absorbing menses comprising the step of contacting the menses with an absorbent article according to the present invention.

BRIEF DESCRIPTION OF THE DRAWINGS

FIG. 1 is a cross section of an absorbent article as indicated by Section 1-1 in FIG. 2.

FIG. 2 is a plan view of the body-facing surface of an absorbent article having a first portion and a second portion.

DETAILED DESCRIPTION OF THE INVENTION

Figure 3:
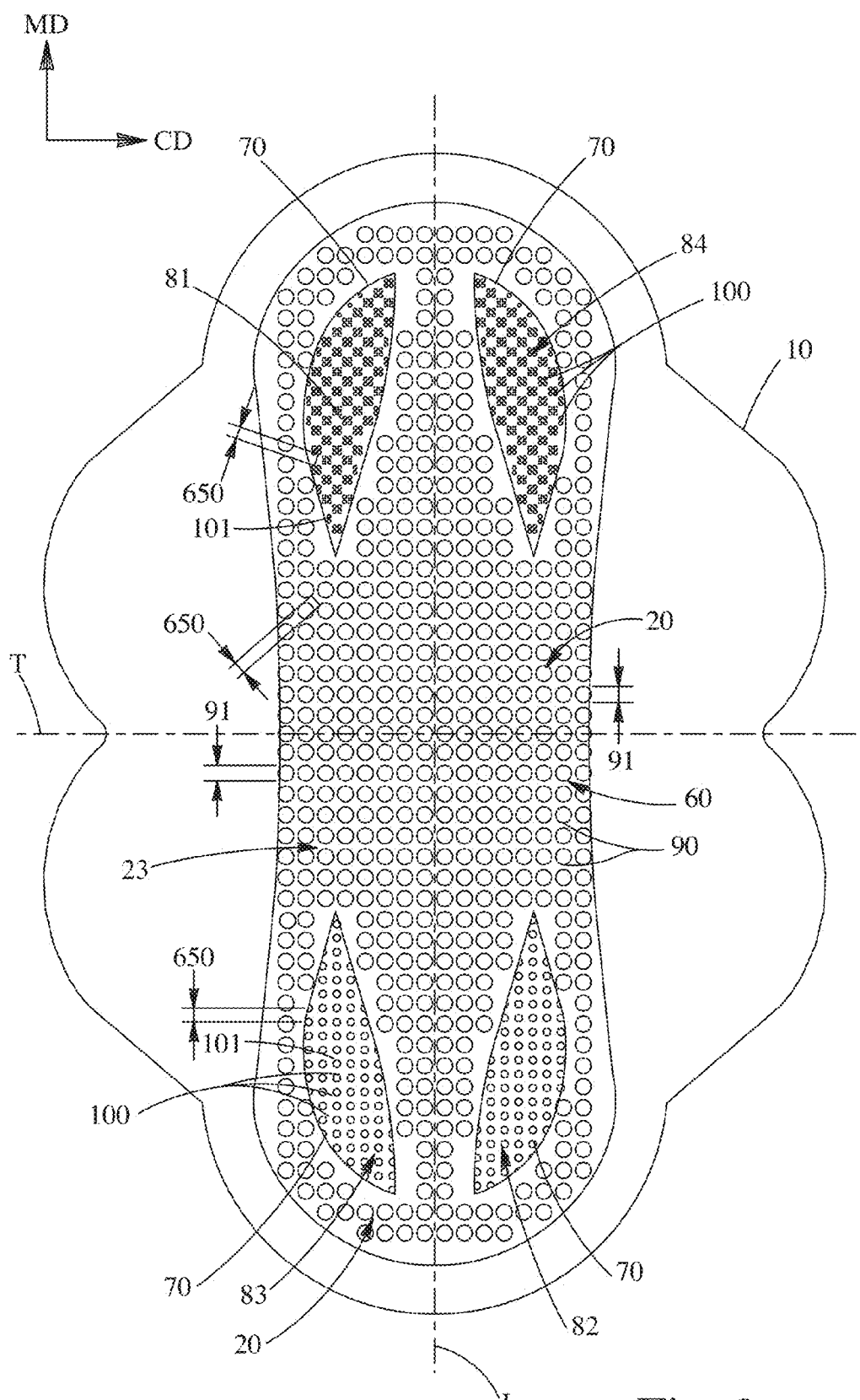
FIG. 3 is a plan view of the body-facing surface of an absorbent article having a first portion and a second portion.

As used herein, "structurally modified", with respect to constituent materials, means that the constituent material (or materials) is altered such that a material that is structurally modified differs in mechanical behavior as compared to the unmodified material. For instance, the structurally modified material can transmit stress (or deform) differently than the unmodified material. The structure of the material can be altered on a molecular level and/or by disrupting the continuity and/or physical arrangement of portions of the material. "Structure" refers to the physical arrangement of the constituent material that governs mechanical behavior (e.g. how stress is transmitted through the material).

As used herein, a structurally modified zone is not a channel. As used herein, a "channel" is an indentation having an in-plane length greater than the width, the length being the longest dimension, curved or straight, within the indentation and the in-plane width being the shortest dimension of the indentation. As used herein, a structurally modified zone does not comprise indentations, dimples, or embossments, i.e., structure created by compressing portions of the absorbent article. A structurally modified zone includes, but is not limited to, apertures and tufts.

As used herein, the word "zone" refers to an area set off as distinct from surrounding or adjoining areas. Thus, for example, a topsheet comprising uniformly spaced apertures, each of which are the same size, over the entire surface of the topsheet cannot be considered to have any zones of apertures. Moreover, for example, in a topsheet comprising uniformly spaced apertures, each of which are the same size, a single aperture and locally surrounding material cannot be considered a zone of apertures because that single aperture and locally surrounding material are not distinct from surrounding or adjoining areas. Similarly, for example, a topsheet comprising uniformly spaced elements, each element being the same, over the entire surface of the topsheet cannot be considered to have any zones of elements. Nor, in a topsheet comprising uniformly spaced elements, for example, may a single element and locally surrounding material be considered a zone. Zones can be separated from one another such that there is an absence of like constructed material between the zones. A zone can comprise an area more than about the product of 5% of the length of the absorbent article and 5% of the width of the absorbent article, the width being measured at the centroid of the respective zone (i.e. the first structurally modified zone, the second structurally modified zone, the third structurally modified zone, and the fourth structurally modified zone).

As used herein, the term "different construction" refers, in one aspect, to the materials used to construct particular portions of the absorbent article or component thereof. For example, a topsheet of an absorbent article can comprise one portion that comprises a nonwoven material and another portion that comprises a thermoplastic film material. In such an example, the topsheet comprises portions having a "different construction". The term "different construction" further refers, in another aspect, to the three-dimensional structure of particular portions of the absorbent article or component thereof. For example, a topsheet of an absorbent article can be made of the same material throughout, but comprise one portion that has been processed to comprise a tufted structure and another portion that has not been so processed and therefore does not comprise a tufted structure. In such an example, the topsheet comprises portions having a "different construction". As another example, a topsheet can be compressed in certain portions to form a channel. In such an example, the topsheet comprises portions having a "different construction".

As used herein, the term "nonwoven web" refers to a web having a structure of individual fibers or threads which are interlaid, but not in a repeating pattern as in a woven or knitted fabric, which do not have randomly oriented fibers. Nonwoven webs or fabrics can be formed from many known processes, such as, for example, air laying processes, meltblowing processes, spunbonding processes, hydroentangling processes, spunlacing processes, and bonded carded web processes. Also, multi-layer webs, such as spunbond-meltblown-spunbond webs and the like made by multiple beam spunbond processes, can be used.

FIG. 1 is an illustration of a cross section of an embodiment of an absorbent article 10 providing for different skin health benefits and fluid acquisition benefits for different portions of the wearer's crotch. The absorbent article 10 can comprise a liquid pervious topsheet 20, a fluid impervious backsheet 30, and an absorbent core 40 disposed between the topsheet 20 and backsheet 30. The topsheet 20 can be a composite topsheet 20 comprised of an upper layer 21 and a lower layer 22 that are engaged with one another in a layered relationship. The topsheet 20 can be described as being in a facing relationship with absorbent core 40.

The absorbent article 10 is discussed herein in the context of what is commonly referred to in the art as a sanitary napkin, menstrual pad, or catamenial pad. It is to be understood that the absorbent article 10 can also be any absorbent article designed to be worn in proximity with the crotch of the wearer. The absorbent article can be a consumer product selected from the group consisting of a sanitary napkin, an adult incontinence product, and a diaper.

The absorbent article 10 and each layer or component thereof can be described as having a body facing surface and a garment facing surface. As can be understood by considering the ultimate use for absorbent articles, such as sanitary napkins, diapers, incontinent products and the like, the body facing surfaces are the surfaces of the layers or components that are oriented closer to the body when in use, and the garment facing surfaces are the surfaces that are oriented closer to the undergarment of the wearer when in use. Therefore, for example, the topsheet 20 has a body facing surface 23 (that can actually be a body contacting surface) and a garment facing surface 24 that can be adhered to an underlying secondary topsheet. The garment facing surface 24 of the backsheet 30, for example, can be oriented closest to, and can contact the wearer's panties in use (via a positioning adhesive 36 if used).

The absorbent article 10 has an absorbent article width measured between the lateral edges 26 measured in the cross direction CD. The absorbent article 10 has a vertical axis H. The absorbent article 10 has a thickness measured in the z-direction.

The topsheet 20 is comprised of a first portion 60 and a second portion 70, wherein the first portion 60 differs in structure from the second portion 70. The second portion 70 can comprise a first structurally modified zone 81. The second portion 70 can comprise a fourth structurally modified zone 84. The first portion 60 and second portion 70 can be comprised of a continuous web of material. The first portion 60 and the second portion 70 can be comprised of the same precursor material or materials. A continuous web of material can be comprised of a single unitary web.

As shown in FIG. 2, the topsheet 20 can have a longitudinal centerline L and a transverse centerline T. Longitudinal centerline L and transverse centerline T define a two-dimensional plane of the topsheet 20 prior to use, which, in the embodiment shown, is associated with the machine direction (MD) and cross machine direction (CD) as is commonly known in the art of making articles using production lines. The absorbent article 10 has a length, which is the longest dimension measured parallel to the longitudinal centerline L. The absorbent article has a width, which is the dimension measured in the CD, e.g., parallel to the transverse centerline T. The transverse centerline T intersects the longitudinal centerline L at mid-length of the longitudinal centerline L. The width of the absorbent article 10 can vary or be substantially constant along the length of the absorbent article 10. For descriptive purposes, the absorbent article 10 has a longitudinal centerline and transverse centerline taken to be coincident with the longitudinal centerline L and transverse centerline T, respectively. The actual longitudinal centerline and the transverse centerline of the absorbent article 10 need not be coincident with the longitudinal centerline L and transverse centerline T of the topsheet 20. The topsheet 20 has a vertical axis that can be taken to be coincident with the vertical axis H of the absorbent article 10. The area 3 of the topsheet 20 is in the MD-CD plane.

Absorbent article 10 can have wings 28, also known as side extensions or flaps, designed to wrap the sides of the crotch region of the panties and attach thereto. Absorbent article 10 and/or wings 28 can have fastening means including attachment components, such as pressure sensitive positioning adhesive 36. The absorbent article 10 can have strips of positioning adhesive 36 on the garment facing surface 24 of the backsheet 30. The positioning adhesive can be hot-melt adhesive material capable of establishing a temporary bond with the undergarment material such as HL-1491 XZP commercially available from H. B. Fuller, Toronto, Ontario, Canada.

The second portion 70 can comprise a first structurally modified zone 81 and a second structurally modified zone 82. The first structurally modified zone 81 and second structurally modified zone 82 can be on opposing sides of the longitudinal centerline L. The first structurally modified zone 81 and the second structurally modified zone 82 can be on opposing sides of an axis parallel to the transverse centerline T. That is, the first structurally modified zone 81 and the second structurally modified zone can be located in diagonally opposing quadrants of the topsheet 20, the quadrants being demarcated by the longitudinal centerline L and an axis parallel to the transverse centerline T. The first structurally modified zone 81 and the second structurally modified zone 82 can be spaced apart from one another.

The second portion 70 can comprise a third structurally modified zone 83 that is disposed on the same side of the longitudinal centerline L as the first structurally modified zone 81, wherein the first structurally modified zone 81 and the third structurally modified zone 83 are disposed on opposing sides of an axis parallel to the transverse centerline T. The first structurally modified zone 81, second structurally modified zone 82, and third structurally modified zone 83 can be spaced apart from one another.

The second portion 70 can comprise a fourth structurally modified zone 84 that is disposed on the same side of the longitudinal centerline L as the second structurally modified zone 82, wherein the second structurally modified zone 82 and the fourth structurally modified zone 84 are disposed on opposing sides of an axis parallel to the transverse centerline T. The first structurally modified zone 81, second structurally modified zone 82, third structurally modified zone 83, and fourth structurally modified zone 84 can be spaced apart from one another.

In an embodiment in which the second portion comprises a first structurally modified zone 81, a second structurally modified zone 82, a third structurally modified zone 83, and a fourth structurally modified zone 84, the structurally modified zones can be spaced apart from one another such that each of the structurally modified zones is individually located in a quadrant of the topsheet 20.

The first portion 60 can comprise the part of the topsheet 20 having a physical structure that differs from the first structurally modified zone 81 and the second structurally modified zone 82. The first portion 60 can comprise the part of the topsheet 20 having a physical structure that differs from the first structurally modified zone 81, the second structurally modified zone 82, the third structurally modified zone 83, and fourth structurally modified zone 84. The second portion 70 can comprise the first structurally modified zone 81 and the second structurally modified zone 82. The second portion 70 can comprise the first structurally modified zone 81, the second structurally modified zone 82, the third structurally modified zone 83, and fourth structurally modified zone 84. That is, the second portion 70 can be that part of the topsheet 20 that is not the first portion 60.

As used herein, one or more of the first structurally modified zone 81, second structurally modified zone 82, third structurally modified zone 83, and fourth structurally modified zone 84 are referred to generically as the structurally modified zone(s). The structurally modified zones can be integral with the topsheet 20. That is, the topsheet 20 is comprised of two or more of the first structurally modified zone 81, second structurally modified zone 82, third structurally modified zone 83, and fourth structurally modified zone 84. The structurally modified zones and first portion 60 can be comprised of a continuous web or webs of material. Each of the structurally modified zones can be comprised of the same precursor materials. The structurally modified zones and the first portion 60 can be comprised of two or more layers engaged with one another in a layered relationship, for example, as in a laminate.

As shown in FIG. 3, the structurally modified zones need not all be the same. For instance, the structures (such as second apertures 100 or other structural features contemplated herein) defining the structurally modified zones can have different sizes and/or be arranged in a different pattern to deliver different performance benefits, such as comfort, to different portions of the body.

In one embodiment, the first structurally modified zone 81, second structurally modified zone 82, third structurally modified zone 83, and fourth structurally modified zone 84 can be separated from one another by at least the maximum dimension (in the plane defined by the longitudinal centerline L and transverse centerline T) of the largest of the structurally modified zones.

By spacing apart the first structurally modified zone 81 and the second structurally modified zone 82, it is thought that different benefits to skin health and fluid acquisition can be targeted to different portions of the wearer's body. If a third structurally modified zone 83 and/or fourth structurally modified zone 84 is present, it is thought that a similar benefit can be obtained by spacing apart the structurally modified zones. For instance, the body facing surface 23 of the topsheet 20 proximal the wearer's anus can have a different texture than the body facing surface 23 of the topsheet 20 proximal to portions of the wearer's body away from the anus. Similarly, the body facing surface 23 of the topsheet 20 proximal the wearer's labia majora can have a different texture than the body facing surface 23 of the topsheet 20 proximal the junction between the wearer's thigh and pubic area. Skin health may also depend on the moisture conditions in and on different regions of the absorbent article associated with wearing the absorbent article. Thus, fluid acquisition and retention of the absorbent article may affect health of the skin. Furthermore, by spacing apart the first structurally modified zone 81, second structurally modified zone 82, third structurally modified zone 83, and fourth structurally modified zone 84, it may be possible to provide for improved fluid handling in the central part of the topsheet while maintaining adequate barrier functions along the lateral sides of the topsheet 20 and the front and rear of the topsheet 20. An additional benefit that may arise is that the first structurally modified zone 81, second structurally modified zone 82, third structurally modified zone 83, and fourth structurally modified zone 84 can be laid out to provide for enhanced comfort about portions of the periphery of the topsheet 20.

The structurally modified zones can comprise more than about 2% of the topsheet area, the area being measured in the plane of the longitudinal centerline L and transverse centerline T of the topsheet 20. The structurally modified zones can comprise more than about 5% of the topsheet area. The structurally modified zones can comprise more than about 10% of the topsheet area. The structurally modified zones can comprise more than about 20% of the topsheet area. The structurally modified zones can comprise more than about 40% of the topsheet area. The structurally modified zones can comprise more than about 60% of the topsheet area.

The first structurally modified zone 81, second structurally modified zone 82, third structurally modified zone 83, and fourth structurally modified zone 84 can have a unique structure as compared to one or more other structurally modified zones. The structurally modified zones can each have the same structure.

The structurally modified zones can comprise macro features. Macro features are elements that are visible to the unaided eye of a person having 20/20 vision from a distance of 30 cm in lighting at least equal to the illumination of a standard 100 watt incandescent white light bulb. Macro features can be elements having an area in the MD-CD plane greater than about 0.25 mm$^2$ Macro features can be elements having an area in the MD-CD plane greater than about 1 mm$^2$ Macro features can be elements having an area in the MD-CD plane greater than about 2 mm$^2$ Macro features can be elements having an area in the MD-CD plane less than about 5 mm². Macro features can be spaced apart from one another by about 1 mm or greater on center.

By way of example and not to be limiting, a macrofeature can be a single aperture, a single tuft, or a single aperture protruding out of the MD-CD plane. Macrofeatures other than tufts, apertures, and apertures protruding out of the MD-CD plane are contemplated. The structurally modified zones can be defined by a plurality of spaced apart macro features, wherein the structurally modified zones are spaced apart from one another by a distance greater than the maximum spacing 650 between adjacent macro features, as shown in FIG. 3.

The structurally modified zones can comprise micro features. Micro features are elements that are not visible to the unaided eye of a person having 20/20 vision from a distance of 30 cm in lighting at least equal to the illumination of a standard 100 watt incandescent white light bulb. The structurally modified zones can be defined by a plurality of spaced apart micro features, wherein the structurally modified zones are spaced apart from one another by a distance greater than the maximum spacing 650 between adjacent micro features. Micro features are smaller than macro features.

By way of example and not to be limiting, a microfeature can be a single aperture, a single tuft, or a single aperture protruding out of the MD-CD plane. Microfeatures other than tufts, apertures, and apertures protruding out of the MD-CD plane are contemplated. By way of example, and not to be limiting, the structurally modified zones can comprise apertures or tufts. Structurally modified zones can comprise other elements or structures that provide for skin health and/or improved fluid acquisition.

The first portion 60 can have first apertures 90 and the second portion 70 can have second apertures 100, as shown in FIG. 3. The second apertures 100 can differ, for example differ in structure, from the first apertures 90. For instance, first apertures 90 and second apertures 100 can be circular opening, the difference being that first apertures 90 and second apertures 100 have a different diameter. Without being bound by theory, it is thought that materials or structurally modified zones having different apertures can interact differently with the wearer's skin. For instance, a topsheet 20 having small apertures may feel softer and be less abrasive to the wearer's skin than a topsheet 20 having large apertures. Similarly, it is thought that materials having one size and shape of apertures may acquire and retain fluid and/or moisture in a manner that differs from materials having another size and/or shape of apertures, which may ultimately provide improved skin health to the wearer. Individual first apertures 90 and second apertures 100 can have an area between about 0.1 mm² and about 4 mm² and any area there between in about 0.1 mm² increments. Individual first apertures 90 and second apertures 100 can have an area of about 0.25 mm², about 1 mm², or about 2 mm² Individual first apertures 90 and second apertures 100 can have an area greater than about 0.25 mm².

The in-plane size of individual second apertures 100 can differ from the in-plane size of individual first apertures 90, as shown in FIG. 3. The size of an aperture is the largest dimension of the aperture in the MD-CD plane (the body facing surface 23 being presented to the viewer of the topsheet). The first apertures 90 have a first size 91 defined by the largest dimension of the first apertures 90 and the second apertures 100 have a second size 101 defined by the largest dimension of the second apertures 100. The second size 101 of the second apertures 100 can differ from the first size 91 of the first apertures 90. The second size 101 of the second apertures 100 can be greater than the first size 91 of the first apertures 90. The second size of the second apertures 100 can be smaller than the first size 91 of the first apertures 90.

Figure 4:
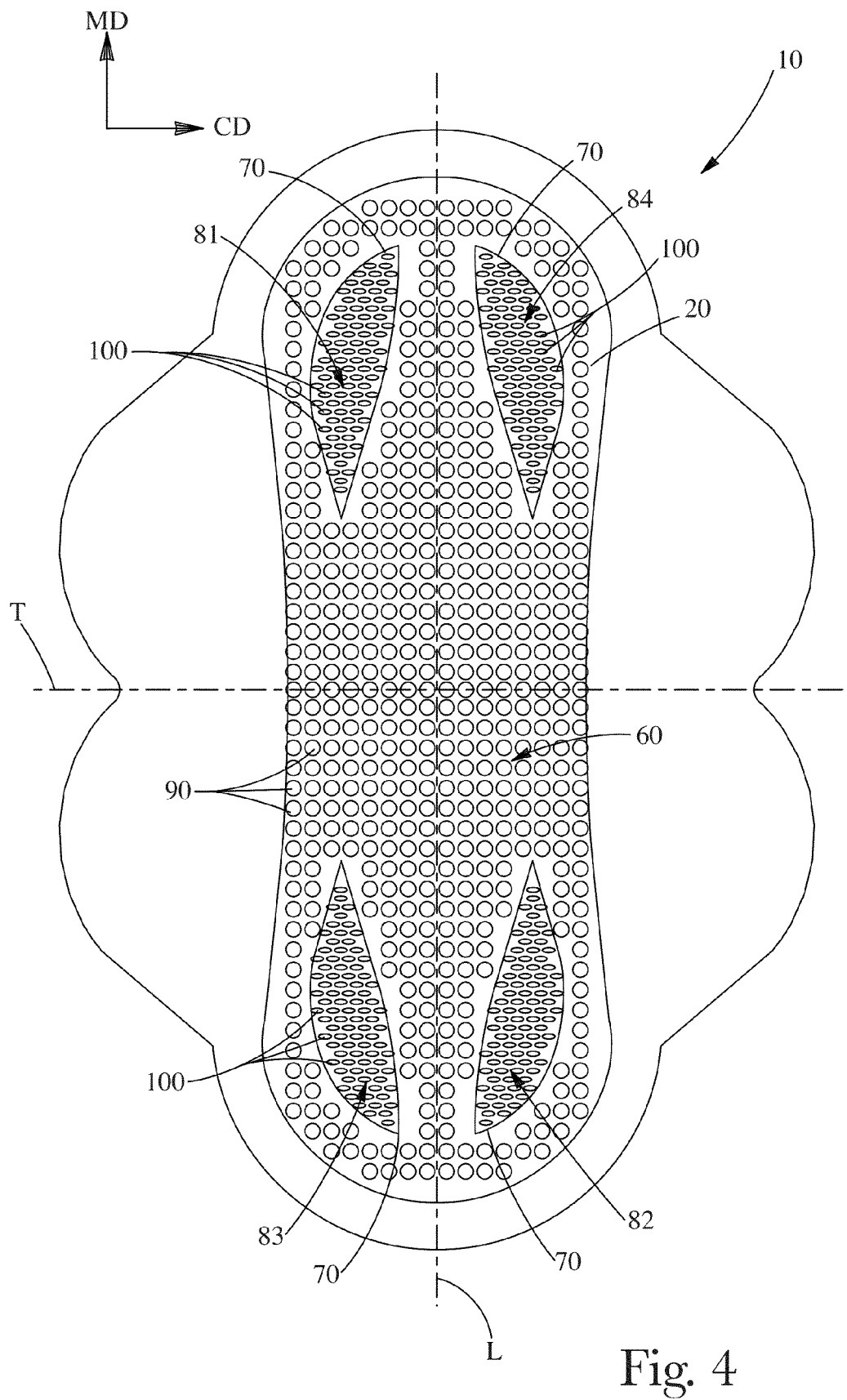
FIG. 4 is a plan view of an absorbent article having a first portion and a second portion.

The in-plane geometry of individual first apertures 90 can differ from the in-plane geometry of individual second apertures 100. In-plane geometry refers to the shape of the object as presented to a viewer looking at the body facing surface 23 of the topsheet 20 so that the MD-CD plane is facing the viewer. For instance, as shown in FIG. 4, first apertures 90 can have a substantially circular shape and the second apertures 100 can have a substantially oval shape. Without being bound by theory, it is thought that the shape of apertures in a material can affect how smooth a material is perceived to be. For instance, materials having oval shaped apertures may feel smoother than materials having circular shaped apertures when the material is stroked by a person in a direction parallel to the major axis of the oval shaped apertures even if the minor axis of the oval shaped apertures and diameter of the circular shaped apertures are about the same. Apertures having an oval shape can have a ratio of major axis dimension to minor axis dimension greater than 1. Apertures having an oval shape can have a ratio of major axis dimension to minor axis dimension greater than about 1.5.

The out of plane geometry of the first portion 60 can differ from the out-of-plane geometry of the second portion 70. The in-plane orientation of the topsheet 20 can be defined by the longitudinal centerline L and the transverse centerline T of the topsheet 20. If the first portion 60 and the second portion 70 comprise apertures, the out-of-plane geometry of individual first apertures 90 can differ from the out-of-plane geometry of individual second apertures 100. Out-of-plane geometry refers the shape presented to a viewer looking at a cross-section of the material orthogonal to the MD-CD plane, with the first portion having a first portion out-of-plane geometry and the second portion having a second portion out-of-plane geometry. Out-of-plane geometry can be sensed visually by an observer. In some instances, the out-of-plane geometry of different portions of the topsheet 20 can provide different tactile sensations. That is, the first portion 60 and second portion 70 of the topsheet 20 can feel different. In the art of garments worn in proximity to the human body, the feel of a material or fabric is referred to as "hand".

Figure 5:
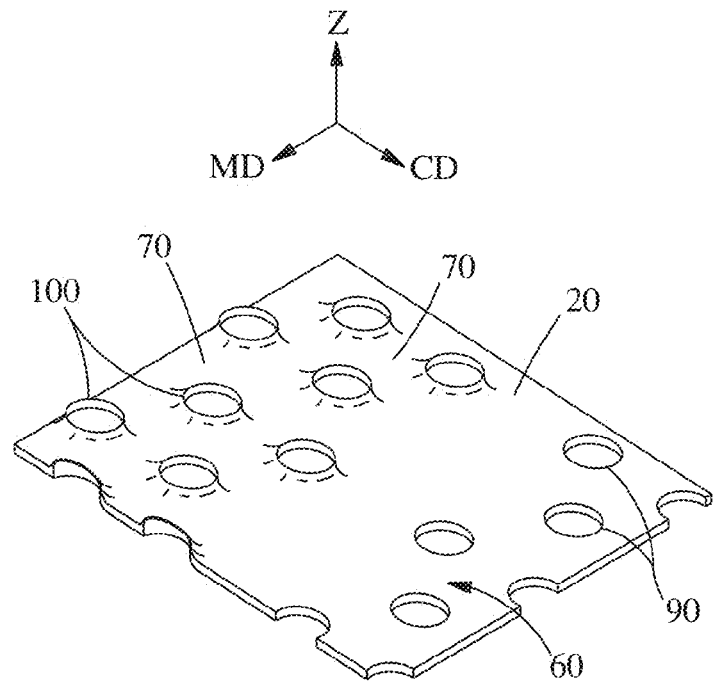
FIG. 5 is a schematic of a portion of a topsheet.

A portion of a topsheet 20 is illustrated in FIG. 5. As shown in FIG. 5, first apertures 90 in the first portion 60 can be substantially flat in the MD-CD plane. Second apertures 100 in the second portion 70 can protrude out of the MD-CD plane in the z direction. Without being bound by theory, a material having apertures protruding out of the MD-CD plane may feel smoother or rougher than a material having apertures in plane, depending on the deformability of the material and the geometry of the out-of-plane protrusion and the geometry of the rim of the aperture.

The first portion can have a first portion aperture area density and the second portion can have a second portion aperture area density. The first portion aperture area density can differ from the second portion aperture area density.

The topsheet 20 can be film, a nonwoven, or a laminate. A laminate topsheet can comprise two layers of film, two layers of nonwoven, or a layer of nonwoven with a film. Apertures can include micro apertures and macro apertures. Macro apertures are apertures that are visible to the unaided eye of a person having 20/20 vision from a distance of 30 cm in lighting at least equal to the illumination of a standard 100 watt incandescent white light bulb. Macro apertures can be elements having an area in the MD-CD plane greater than about 0.25 mm² Micro apertures are apertures that are not visible to the unaided eye of a person having 20/20 vision from a distance of 30 cm in lighting at least equal to the illumination of a standard 100 watt incandescent white light bulb. Micro apertures and/or other texturing can be formed prior to processing as described herein.

Figure 6:
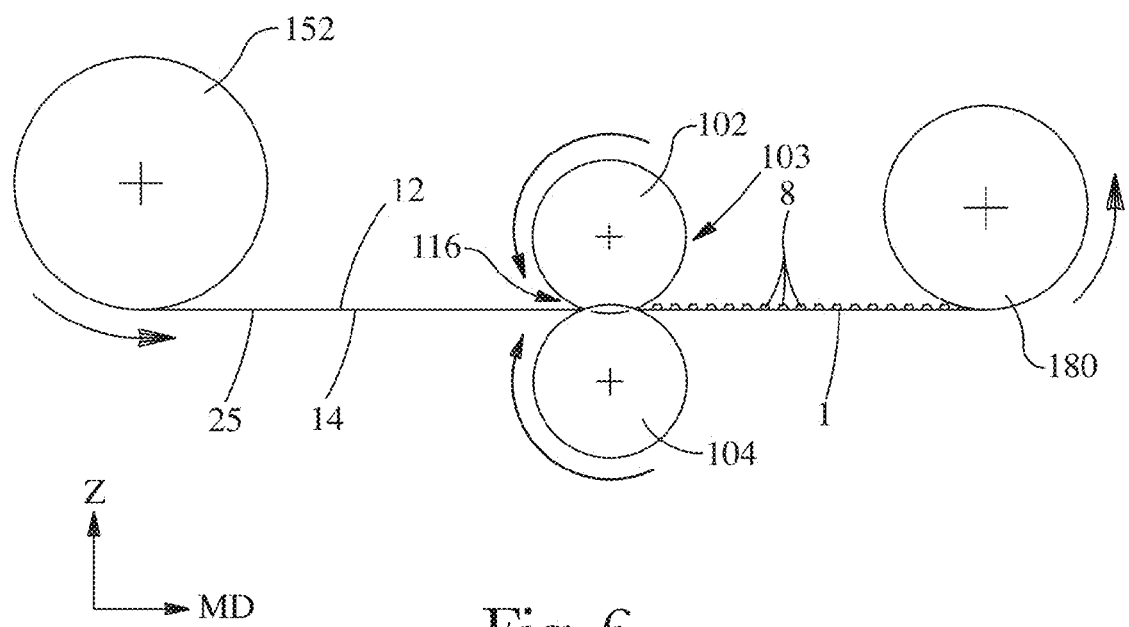
FIG. 6 is a schematic of an apparatus for forming a web having apertures.

An apertured web 1, which can be used as a topsheet 20, can be formed as shown in FIG. 6. As shown in FIG. 6, web 1 can be formed from a generally planar, two dimensional precursor web 25 having a first side 12 and a second side 14. Precursor web 25 can be, for example, a polymer film, a nonwoven web, a woven fabric, a paper web, a tissue paper web, or a knitted fabric, or a multilayer laminate of any of the aforementioned. In general, the term "side" is used herein in the common usage of the term to describe the two major surfaces of generally two-dimensional webs, such as paper and films. In a composite or laminate structure, the first side 12 of the web 1 is the first side of one of the outermost layers or plies, and the second side 14 is the second side of the other outermost layer or ply.

Precursor web 25 can be a polymeric film web. Polymeric film webs can be deformable. Deformable, as used herein, describes a material which, when stretched beyond its elastic limit, will substantially retain its newly formed conformation. Such deformable materials may be chemically homogeneous or heterogeneous, such as homopolymers and polymer blends, structurally homogeneous or heterogeneous, such as plain sheets or laminates, or any combination of such materials.

Deformable polymeric film webs that can be used can have a transformation temperature range in which changes in the solid state molecular structure of the material occur. Changes in the structure can include a change in crystalline structure and/or a change from solid to molten state. As a consequence, above the transformation temperature range, certain physical properties of the material are substantially altered. For a thermoplastic film, the transformation temperature range is the melt temperature range of the film, above which the film is in a molten state and loses substantially all previous thermomechanical history.

Polymeric film webs can comprise thermoplastic polymers having characteristic rheological properties which depend on their composition and temperature. Below their glass transition temperature, such thermoplastic polymers can be hard, stiff, and/or brittle. Below the glass transition temperature, the molecules are in rigid, fixed positions. Above the glass transition temperature but below the melt temperature range, thermoplastic polymers exhibit viscoelasticity. In this temperature range, the thermoplastic material generally has a certain degree of crystallinity, and is generally flexible and to some degree deformable under a force. The deformability of such a thermoplastic is dependent on the rate of deformation, amount (dimensional quantity) of deformation, length of time it is deformed, and its temperature. In one embodiment, processes can be utilized to form materials comprising thermoplastic polymers, especially thermoplastic film, which are within this viscoelastic temperature range.

Polymeric film webs can comprise a certain amount of ductility. Ductility, as used herein, is the amount of permanent, unrecoverable, plastic strain which occurs when a material is deformed, prior to failure (rupture, breakage, or separation) of the material. Materials that can be used as described herein can have a minimum ductility of at least about 10%, or at least about 50%, or at least about 100%, or at least about 200%.

Polymeric film webs can include materials normally extruded or cast as films such as polyolefins, nylons, polyesters, and the like. Such films can be thermoplastic materials such as polyethylene, low density polyethylene, linear low density polyethylene, polypropylenes and copolymers and blends containing substantial fractions of these materials. Such films can be treated with surface modifying agents to impart hydrophilic or hydrophobic properties, such as imparting a lotus effect. As noted below, polymeric film webs can be textured or otherwise altered from a strictly flat, planar configuration.

Precursor web 25 can be a nonwoven web. For nonwoven precursor webs 25, the precursor web 25 can comprise unbonded fibers, entangled fibers, tow fibers, or the like. Fibers can be extensible and/or elastic, and may be pre-stretched for processing. Fibers of precursor web 25 can be continuous, such as those produced by spunbonded methods, or cut to length, such as those typically utilized in a carded process. Fibers can be absorbent, and can include fibrous absorbent gelling materials. Fibers can be bicomponent, multiconstituent, shaped, crimped, or in any other formulation or configuration known in the art for nonwoven webs and fibers.

Nonwoven precursor webs 25 can be any known nonwoven webs comprising polymer fibers having sufficient elongation properties to be formed into apertured web 1. In general, the polymeric fibers can be bondable, either by chemical bond (e.g. by latex or adhesive bonding), pressure bonding, or thermal bonding. If thermal bonding techniques are used in the bonding process described below, a certain percentage of thermoplastic material, such as thermoplastic powder or fibers can be used to facilitate thermal bonding of portions of fibers in the web, as discussed more fully below. Nonwoven precursor web 25 can comprise about 100% by weight thermoplastic fibers. Nonwoven precursor web 25 can comprise as little as about 10% by weight thermoplastic fibers. Likewise, nonwoven precursor web 25 can comprise any amount by weight thermoplastic fibers in 1% increments between about 10% and about 100%.

Precursor web 25 can be a composite or a laminate of two or more precursor webs, and can comprise two or more nonwoven webs or a combination of polymer films, nonwoven webs, woven fabrics, paper webs, tissue webs, or knitted fabrics. Precursor web 25 can be supplied from a supply roll 152 (or supply rolls, as needed for multiple web laminates) or any other supply means, such as festooned webs, as is known in the art. In one embodiment, precursor web 25 can be supplied directly from a web making apparatus, such as a polymer film extruder or a nonwoven web-making production line.

The total basis weight of precursor web 25 (including laminate or multi-layer precursor webs 25) can range from about 8 gsm to about 500 gsm, depending on the ultimate use of the web 1, and can be produced in 1 gsm increments between about 8 and about 500 gsm. The constituent fibers of nonwoven precursor web 25 can be polymer fibers, and can be monocomponent, bicomponent and/or biconstituent fibers, hollow fibers, non-round fibers (e.g., shaped (e.g., trilobal) fibers or capillary channel fibers), and can have major cross-sectional dimensions (e.g., diameter for round fibers, long axis for elliptical shaped fibers, longest straight line dimension for irregular shapes) ranging from about 0.1 to about 500 microns in 0.1 micron increments.

Precursor web 25 can be preheated by means known in the art, such as by radiant heating, forced air heating, convection heating, or by heating over oil-heated rollers. Precursor web 25 can be treated with coatings, such as with surfactants, lotions, adhesives, and the like. Treating precursor web 25 can be achieved by means known in the art such as by spraying, slot coating, extruding, or otherwise applying coatings to one or both surfaces.

Supply roll 152 rotates in the direction indicated by the arrow in FIG. 6 as precursor web 25 is moved in the machine direction by means known in the art, including over or around any of various idler rollers, tension-control rollers, and the like to the nip 116 of a pair of counter-rotating rolls 102 and 104. The rolls 102 and 104 can comprise forming apparatus 103. The pair of rolls 102 and 104 can operate to form volcano shaped structures 8 and apertures in precursor web 25. Apertured web 1 can be taken up on wind up roll 180.

There are a variety of approaches for creating apertures in webs. Factors that can influence the approach selected for creating apertures include, but are not limited to, whether the precursor web 25 is a nonwoven or polymeric film, the desired geometry of the aperture, the desired processing speed, and the amount of control of the process that is desired.

An approach for forming apertures in polymeric film webs and nonwoven webs is to employ a pair of intermeshing rolls as disclosed in U.S. patent application Ser. No. 11/249,618 by O'Donnell et al. and U.S. application Ser. No. 12/188,543 filed Aug. 8, 2008.

The aperture area density can be varied from about 1 aperture/cm$^2$ to about 6 apertures/cm$^2$ to about 60 apertures/cm$^2$, in increments of 1 aperture/cm$^2$. There can be, for example, at least about 10 apertures/cm$^2$, or at least about 25 apertures/cm$^2$.

Figure 7:
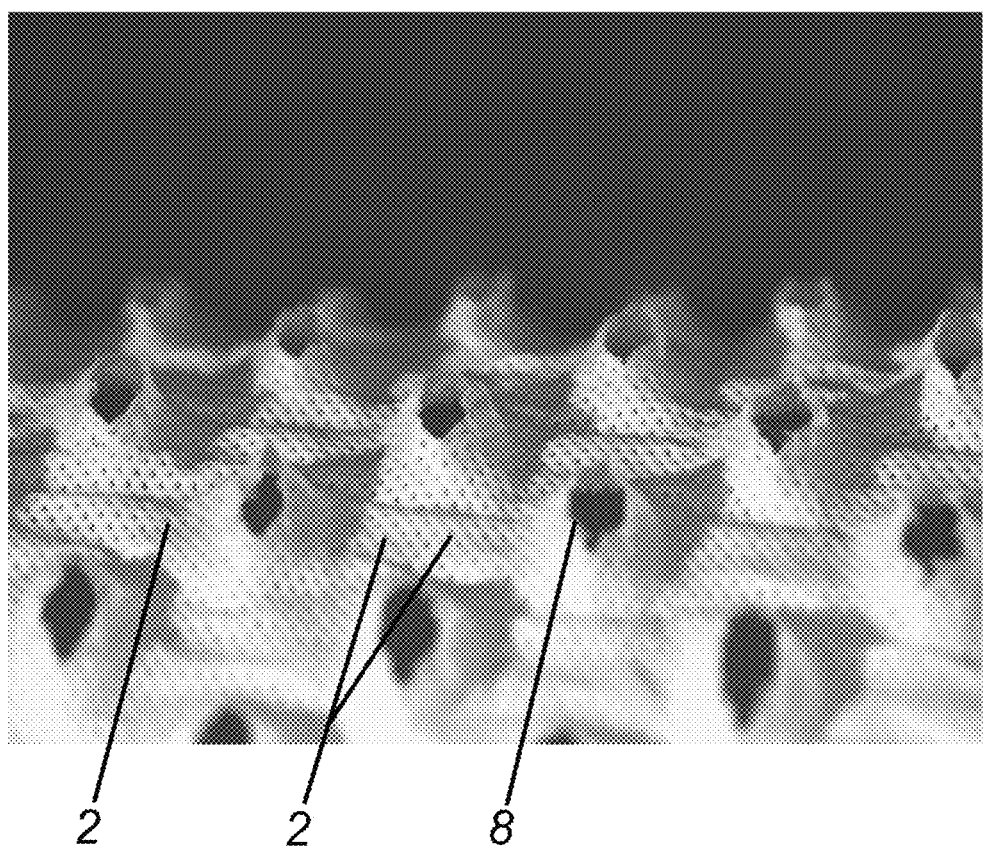
FIG. 7 is an image of a truncated generally conically shaped apertures and aberrations.

FIG. 7 shows an embodiment of a three-dimensional apertured web 1 in which the precursor web 25 was not a flat film but rather was a film that was pre-textured with microscopic aberrations 2. Aberrations 2 can be bumps, embossments, holes, or the like. In the embodiment shown, aberrations 2 are volcano-shaped micro-apertures, formed by a hydroforming process. A suitable hydroforming process is the first phase of the multiphase hydroforming process disclosed in U.S. Pat. No. 4,609,518, issued to Curro et al. on Sep. 2, 1986. The hydroforming screen utilized for the web shown in FIG. 7 was a "100 mesh" screen and the film was obtained from Tredegar Film Products, Terre Haute, Ind. Apertures, defined by the rims of the truncated generally conical shaped structures 8, can be formed by teeth 110 of roll 104 in forming apparatus 103. The truncated generally conical shaped structures 8 can be oriented in a topsheet 20 such that the rims of the truncated generally conical shaped structures are on the body facing side of the topsheet. The truncated generally conical shaped structures 8 can be oriented in a topsheet 20 such that the rims of the truncated generally conical shaped structures are on the garment facing side of the topsheet 20. The truncated generally conical shaped structures 8 can be oriented in a topsheet 20 such that some of the rims of the truncated generally conical shaped structures are on the garment facing side of the topsheet 20 and some of the rims of the truncated generally conical shaped structures are on the body facing side of the topsheet 20. A polymeric web, such as that employed in Always Ultra sanitary napkins, marked by Procter & Gamble Co., Cincinnati, Ohio, or that disclosed in U.S. Pat. No. 7,402,723, issued to Stone et al., Jul. 22, 2008, can be practical for the topsheet 20 or components/portions thereof.

Aberrations 2 can also be non-apertured protrusions or hollow fibrils having an open proximal end and a closed distal end integral with the precursor web 25 to provide texture that provides for a tactile impression of softness. Aberrations 2 other than non-apertured protrusions and fibrils are contemplated. Softness can be beneficial when webs 1 are used as a topsheet in a disposable absorbent article. A soft, compliant topsheet for a disposable absorbent article can be achieved when the apertured web 1 is used with the second side 14 having aberrations 2 as the body-facing surface of the article. In some embodiments, aberrations 2 can be on the garment facing side of the topsheet to possibly provide for a different level of comfort or different properties related to flow of fluids.

The topsheet 20 can comprise an apertured nonwoven web. U.S. patent application Ser. No. 11/249,618, U.S. Pat. No. 5,714,107, and U.S. Pat. No. 5,628,097 disclose apertured nonwoven webs, as well as apparatuses and methods for creating apertures in nonwoven webs.

The nonwoven precursor web 25 may be extensible, elastic, or nonelastic. The nonwoven precursor web 25 may be a spunbonded web, a meltblown web, or a bonded carded web. If the nonwoven precursor web 25 is a web of meltblown fibers, it may include meltblown microfibers. The nonwoven precursor web 25 may be made of fiber forming polymers such as, for example, polyolefins. Exemplary polyolefins include one or more of polypropylene, polyethylene, ethylene copolymers, propylene copolymers, and butene copolymers.

In another embodiment, the nonwoven precursor web 25 may be a multilayer material having, for example, at least one layer of a spunbonded web joined to at least one layer of a meltblown web, a bonded carded web, or other suitable material. For example, the nonwoven precursor web 25 may be a multilayer web having a first layer of spunbonded polypropylene having a basis weight from about 0.2 to about 8 ounces per square yard, a layer of meltblown polypropylene having a basis weight from about 0.2 to about 4 ounces per square yard, and a second layer of spunbonded polypropylene having a basis weight from about 0.2 to about 8 ounces per square yard. Alternatively, the nonwoven web may be a single layer of material, such as, for example, a spunbonded web having a basis weight from about 0.2 to about 10 ounces per square yard or a meltblown web having a basis weight from about 0.2 to about 8 ounces per square yard.

The nonwoven precursor web 25 may be joined to a polymeric film to form a laminate. Suitable polymeric film materials include but are not limited to polyolefins, such as polyethylenes, polypropylene, ethylene copolymers, propylene copolymers, and butene copolymers; nylon (polyamide); metallocene catalyst-based polymers; cellulose esters; poly (methyl methacrylate); polystyrene; poly (vinyl chloride); polyester; polyurethane; compatible polymers; compatible copolymers; and blends, laminates and/or combinations thereof.

The nonwoven precursor web 25 may also be a composite made up of a mixture of two or more different fibers or a mixture of fibers and particles. Such mixtures may be formed by adding fibers and/or particulates to the gas stream in which the meltblown fibers or spunbond fibers are carried so that an intimate entangled co-mingling of fibers and other materials, e.g., wood pulp, staple fibers, and particles, occurs prior to collection of the fibers.

The nonwoven precursor web 25 of fibers can be joined by bonding to form a coherent web structure. Suitable bonding techniques include, but are not limited to, chemical bonding, thermobonding, such as point calendering, hydroentangling, and needling.

Other structures of incremental stretching mechanisms suitable for incrementally stretching or tensioning the nonwoven web are described in International Patent Publication No. WO 95/03765, published Feb. 9, 1995, in the name of Chappell, et al.

The nonwoven apertured web can be taken up on wind-up roll and stored. Alternatively, the nonwoven apertured web may be fed directly to a production line where it is used to form a topsheet on a disposable absorbent article.

Figure 8:
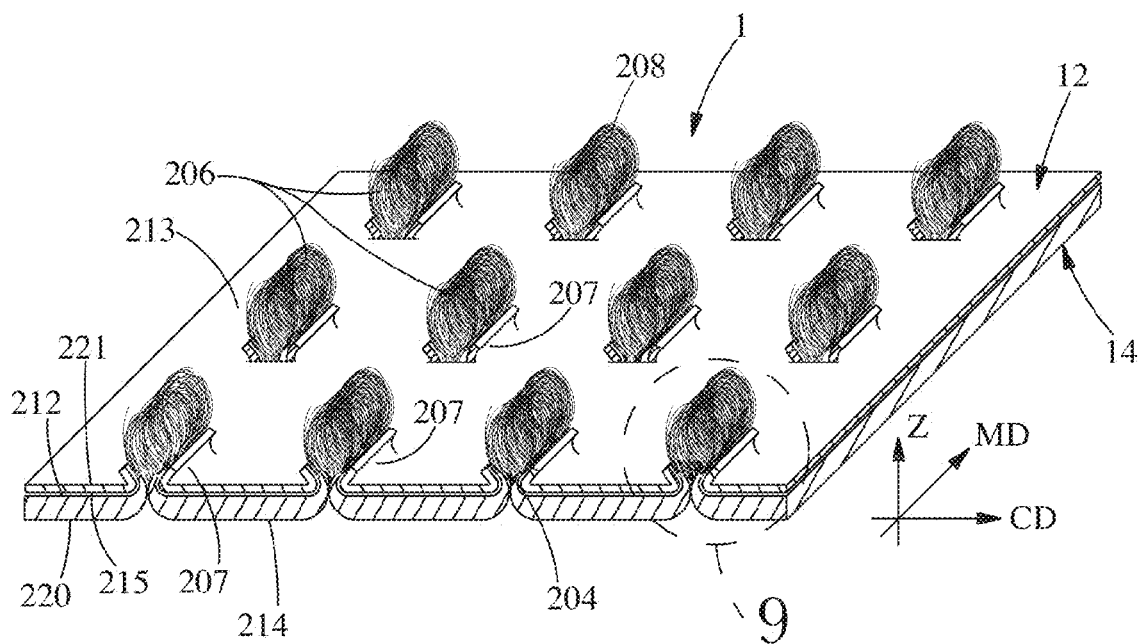
FIG. 8 is a schematic of a web having tufts.

The first portion 60 and/or the second portion 70 can comprise tufts 206 illustrated in FIG. 8. Tufts 206 can comprise a laminate web 1 comprised of two or more layers in which one of the layers is pushed into the other layer or protrudes through apertures in the other layer, an example of which is shown in FIG. 8. The layers are referred to herein as generally planar, two-dimensional precursor webs, such as first precursor web 220 and second precursor web 221. Either precursor web can be a film, a nonwoven, or a woven web. First precursor web 220 and second precursor web 221 (and any additional webs) can be joined with or without adhesive, thermal bonding, ultrasonic bonding and the like. First precursor web 220 and second precursor web 221 can correspond to the lower layer 22 and upper layer 21, respectively, of topsheet 20, as shown in FIG. 1.

Web 1 has a first side 12 and a second side 14, the term "sides" being used in the common usage of generally planar two-dimensional webs, such as paper and films that have two sides when in a generally flat condition. First precursor web 220 has a first precursor web first surface 212 and a first precursor web second surface 214. Second precursor web 221 has a second precursor web first surface 213 and a second precursor web second surface 215. Web 1 has a machine direction (MD) and a cross machine direction (CD) as is commonly known in the art of web manufacture. The first precursor web 220 can be a nonwoven web comprised of substantially randomly oriented fibers, a polymer film, or a woven web. By "substantially randomly oriented" is meant that, due to processing conditions of the precursor web, there may be a higher amount of fibers oriented in the MD than the CD, or vice-versa. Second precursor web 221 can be a nonwoven web similar to the first precursor web 220, or a polymer film or an apertured polymer film, such as a polyethylene film.

Figure 9:
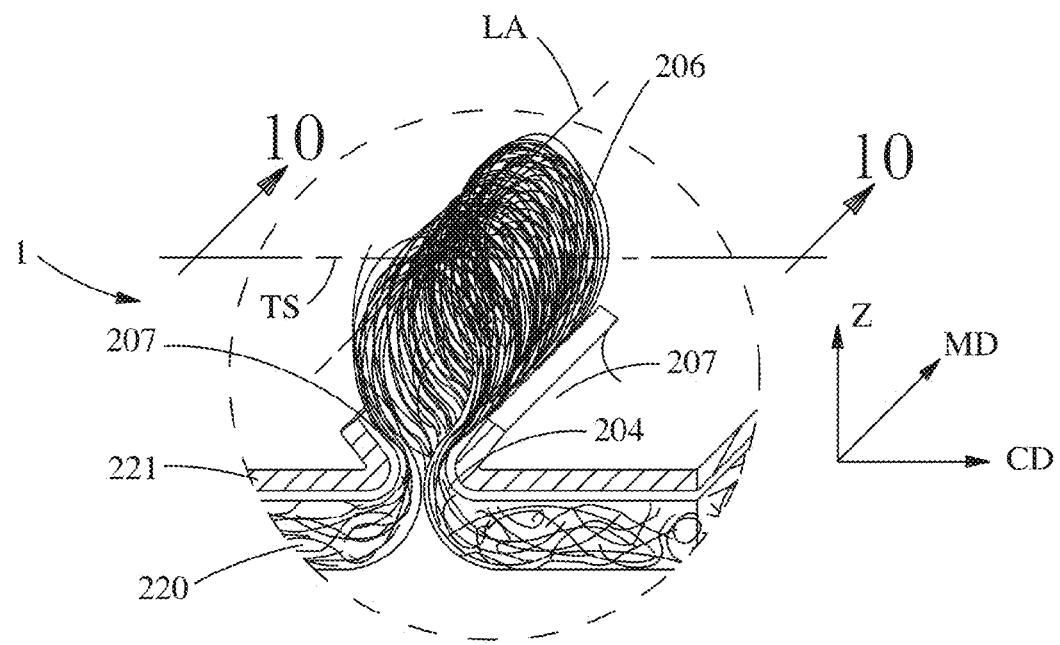
FIG. 9 is a cutaway section of a web having tufts as indicated by Cutaway 17 in FIG. 8.

In one embodiment, first side 12 of web 1 is defined by exposed portions of the second precursor web first surface 213 and one or more discrete tufts 206, which can be discrete tufts 206, which are integral extensions of the fibers of a nonwoven first precursor web 220. Tufts 206 can protrude through apertures in the second precursor web 221. As shown in FIG. 9, each tuft 206 can comprise a plurality of looped fibers 208 extending through second precursor web 221 and outwardly from the second precursor web first surface 213 thereof.

Tufts can be formed by urging fibers out-of-plane in the z-direction at discrete, localized, portions of first precursor web 220.

First precursor web 220 can be a fibrous woven or nonwoven web comprising elastic or elastomeric fibers. Elastic or elastomeric fibers can be stretched at least about 50% and return to within 10% of their original dimension. Tufts 206 can be formed from elastic fibers if the fibers are simply displaced due to the mobility of the fiber within the nonwoven, or if the fibers are stretched beyond their elastic limit and are plastically deformed.

Second precursor web 221 can be virtually any web material, the only requirement being that it have sufficient integrity to be formed into the laminate by the process described below, and that it have elongation properties relative to first precursor web 220, such that upon experiencing the strain of fibers from first precursor web 220 being urged out-of-plane in the direction of second precursor web 221, second precursor web 221 will be urged out of plane (e.g. by stretching) or rupture (e.g. by tearing due to extensional failure). If rupture occurs, IPS apertures 204 can be formed at the rupture locations (IPS stands for Inter-Penetrating Self). Portions of first precursor web 220 can extend through IPS apertures 204 (i.e., "push through" or protrude through) in second precursor web 221 to form tufts 206 on first side 12 of web 1. In one embodiment second precursor web 221 is a polymer film. Second precursor web 221 can also be a woven textile web, a nonwoven web, a polymer film, an apertured polymer film, a paper web, (e.g., tissue paper), a metal foil (e.g., aluminum wrapping foil), a foam (e.g., urethane foam sheeting), or the like.

As shown in FIGS. 8 and 9, tufts 206 can extend through IPS apertures 204 in second precursor web 221. IPS apertures 204 can be formed by locally rupturing second precursor web 221. Rupture may involve a simple splitting open of second precursor web 221, such that IPS apertures 204 are in-plane (MD-CD) two-dimensional apertures. However, for some materials, such as polymer films, portions of second precursor web 221 can be deflected or urged out-of-plane (i.e., the plane of second precursor web 221) to form flap-like structures, referred to herein as a flap, or flaps, 207. The form and structure of flaps 207 can be dependent upon the material properties of second precursor web 221. Flaps 207 can have the general structure of one or more flaps, as shown in FIGS. 8 and 9. In other embodiments, flap 207 can have a more volcano shaped structure, as if the tuft 206 is erupting from the flap 207.

Tufts 206 can be, in a sense, "pushed through" (or protrude through) second precursor web 221 and can be "locked" in place by frictional engagement with IPS apertures 204. This indicates a certain amount of recovery at the opening that tends to constrain tuft 206 from pulling back out through IPS apertures 204. The frictional engagement of the tufts and openings can provide for a laminate web structure having tufting on one side that can be formed without adhesives or thermal bonding.

Tufts 206 can be spaced sufficiently closely so as to substantially cover (for example cover more than about 85% the area, fraction portion, or zone of interest) first side 12 of web 1 when tufts 206 protrude through second precursor web 221. In such an embodiment, both sides of web 1 appear to be nonwoven, with a difference between first side 12 and second side 14 being a difference in surface texture. Therefore, in one embodiment, the web 1 can be described as a laminate material of two or more precursor webs, wherein both sides of the laminate web are substantially covered by fibers from only one of the precursor webs.

The looped fibers 208 can be substantially aligned such that tuft 206 has a distinct linear orientation and a long axis LA, as shown in FIG. 9. Tufts 206 can also have a short axis TS generally orthogonal to long axis LA in the MD-CD plane the MD-CD plane able to be considered as encompassing the first precursor web 220 and second precursor web 221 and tufts 206). In the embodiment shown in FIGS. 9 and 10, long axis LA is parallel to the MD. The tuft 206 can have a symmetrical shape in the MD-CD plane, such as a circular shape or square shape. Tufts 206 can have an aspect ratio (ratio of longest dimension to shortest dimension, both measured in the MD-CD plane) greater than 1. In one embodiment, all the spaced apart tufts 206 have generally parallel long axes LA. The number of tufts 206 per unit area of web 1, i.e., the area density of tufts 206, can be varied from about 1 tuft/cm$^2$ to about 100 tufts/cm$^2$. There can be at least about 10, or at least about 20 tufts/cm$^2$.

Figure 10:
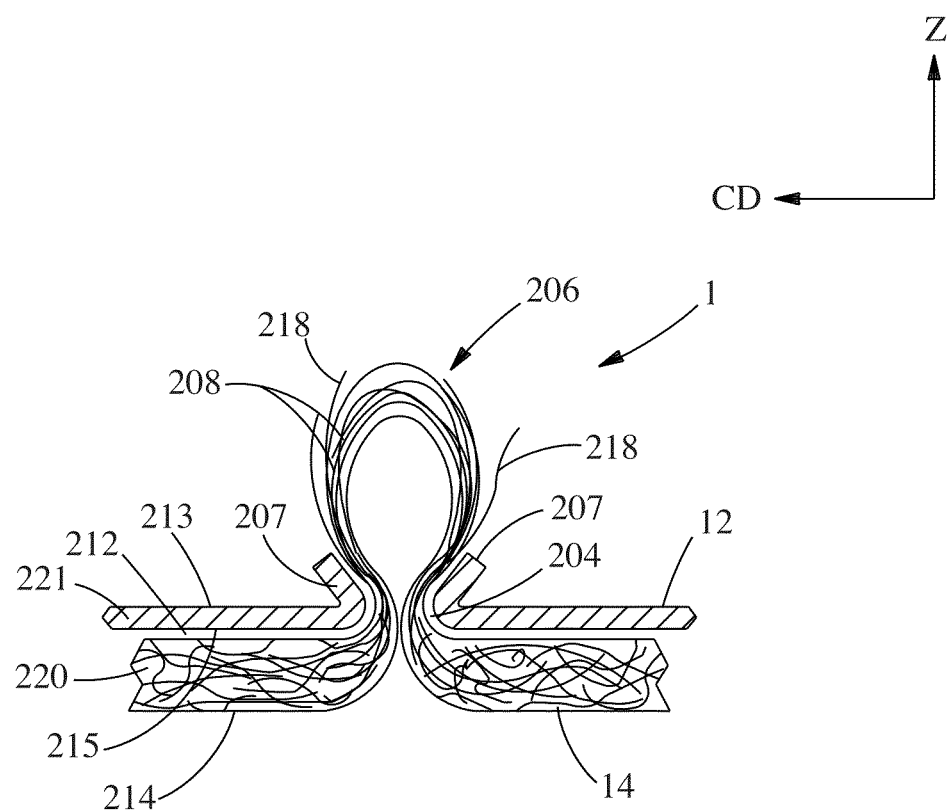
FIG. 10 is a cross section of a web having tufts as indicated by Section 18-18 in FIG. 9.

In another embodiment, each tuft 206 can comprise a plurality of non-looped fibers 218 (as shown in FIG. 10) that extend outwardly from the second precursor web first surface 213. In general, the looped fibers 208 or non-looped fibers 218 of the tufts 206 comprise fibers that are integral with and extend from the fibers of the first precursor web 220.

The process and apparatus for forming tufts 206 is similar in many respects to a process described in U.S. Pat. No. 5,518,801 entitled "Web Materials Exhibiting Elastic-Like Behavior" and referred to in subsequent patent literature as "SELF" webs, which stands for "Structural Elastic-like Film". As described below, the teeth 110 of roll 104 have a geometry associated with the leading and trailing edges that permit the teeth to essentially "push" through the plane of the first precursor web 220 and second precursor web 221. In a two layer laminate web, the teeth 110 urge fibers from a first precursor web 220 simultaneously out-of-plane and through the plane of second precursor web 221. Therefore, tufts 206 of web 1 can be "tunnel-like" tufts of looped fibers 208 extending through and away from the second precursor web first surface 213 and can be symmetrically shaped.

In one embodiment, second precursor web 221 has an elongation to break in the range of 1%-5%. While the actual required elongation to break depends on the strain to be induced to form web 1, it is recognized that in some embodiments, second precursor web 221 can exhibit a web elongation-to-break of about 6%, about 7%, about 8%, about 9%, about 10%, or more. It is also recognized that actual elongation-to-break can depend on the strain rate, which is a function of line speed. Elongation to break of webs can be measured by means known in the art, such as by standard tensile testing methods using standard tensile testing apparatuses, such as those manufactured by Instron, MTS, Thwing-Albert, and the like.

Furthermore, relative to first precursor web 220, second precursor web 221 can have lower fiber mobility (if any) and/or lower elongation-to-break (i.e., elongation-to-break of individual fibers, or, if a film, elongation-to-break of the film) such that, rather than extending out-of-plane to the extent of the tufts 206, second precursor web 221 can fail in tension under the strain produced by the formation of tufts 206, e.g., by the teeth 110 of forming apparatus 103. In one embodiment, second precursor web 221 exhibits sufficiently low elongation-to-break relative to first precursor web 220 such that flaps 207 of IPS apertures 204 only extend slightly out-of-plane, if at all, relative to tufts 206. Second precursor web 221 can have an elongation to break of at least about 10% less than the first precursor web 220, or at least about 30% less, or at least about 50% less, or at least about 100% less than that of first precursor web 220.

The number, spacing, and size of tufts 206 can be varied by changing the number, spacing, and size of teeth 110 and making corresponding dimensional changes as necessary to roll 104 and/or roll 102. This variation, together with the variation possible in first precursor web 220 and second precursor web 221 permits many varied webs 1 to be made for many purposes such as personal care items, as disclosed in WO 01/76523. A web 1 comprising a nonwoven/film first precursor web/second precursor web combination can also be used as a component in disposable absorbent articles.

A tufted web 1 can be formed from a nonwoven first precursor web 220 having a basis weight of between about 60 gsm and 100 gsm (80 gsm being practical) and a polyolefinic film (e.g., polyethylene or polypropylene) second precursor web 221 having a density of about 0.91-0.94 g/cm³ and a basis weight of about 20 gsm.

Web 1 having tufts 206 can be used as a topsheet 20 or a portion of topsheet 20 of absorbent article 10. Web 1 having tufts 206 can be beneficial as a topsheet 20 for absorbent articles due to the combination of excellent fluid acquisition and distribution to the absorbent core 40, and excellent prevention of rewet to the body-facing surface of topsheet 20 when in use. Rewet can be a result of at least two causes: (1) squeezing out of the absorbed fluid due to pressure on the absorbent article 10; and/or (2) wetness entrapped within or on the topsheet 20.

Surface texture in various portions of the topsheet 20 can be created by providing tufts 206. Tufts 206 can be oriented such that tufts 206 comprise a portion of the body facing surface 23 of the topsheet 20. Tufts 206 can be oriented such that tufts 206 are oriented on the garment facing surface of the topsheet 20.

A topsheet 20 can be made by using a nonwoven first precursor web 220 and a fluid impermeable or fluid permeable polyethylene film second precursor web 221. The basis weights of the component webs can be varied, however, in general due to cost and benefit considerations a total basis weight of between about 20 gsm and 80 gsm can be desirable for web 1. When made as a film/nonwoven laminate, web 1 can combine the softness and fluid capillarity of fiber tufts and the rewet prevention of a fluid impermeable polymer film.

The first portion 60 can comprise tufts 206. The second portion 70 can comprise tufts 206. The first portion 60 and the second portion 70 can both comprise tufts 206, wherein the tufts in the first portion 60 differ from the tufts in the second portion 70. The difference in the tufts 206 can be the size of the tuft in the out-of-plane dimension, z. The difference in the tufts 206 can be the size or shape of the tuft in the MD-CD plane. The size of a tuft is the largest dimension of the tuft in a plane parallel to the MD-CD plane (presented to the viewer of the topsheet). The difference in the tufts 206 can be the form of the tuft 206 with respect to whether or not the tuft 206 protrudes through the second precursor web 221 or is nested within second precursor web 221. The difference in the tufts 206 can be the color of the tufts 206. Different colors of tufts 206 can help the wearer understand that different portions of the absorbent article 10 may perform differently, help her position the absorbent article 10 properly in her panty, and provide for emotional confidence.

In one example embodiment, the absorbent core 40 can be between a laminate web comprising first precursor web 220 and second precursor web 221 such that neither the first precursor web 220 nor the second precursor web 221 or a part of either web is between the absorbent core 40 and backsheet 30.

Figure 11A:
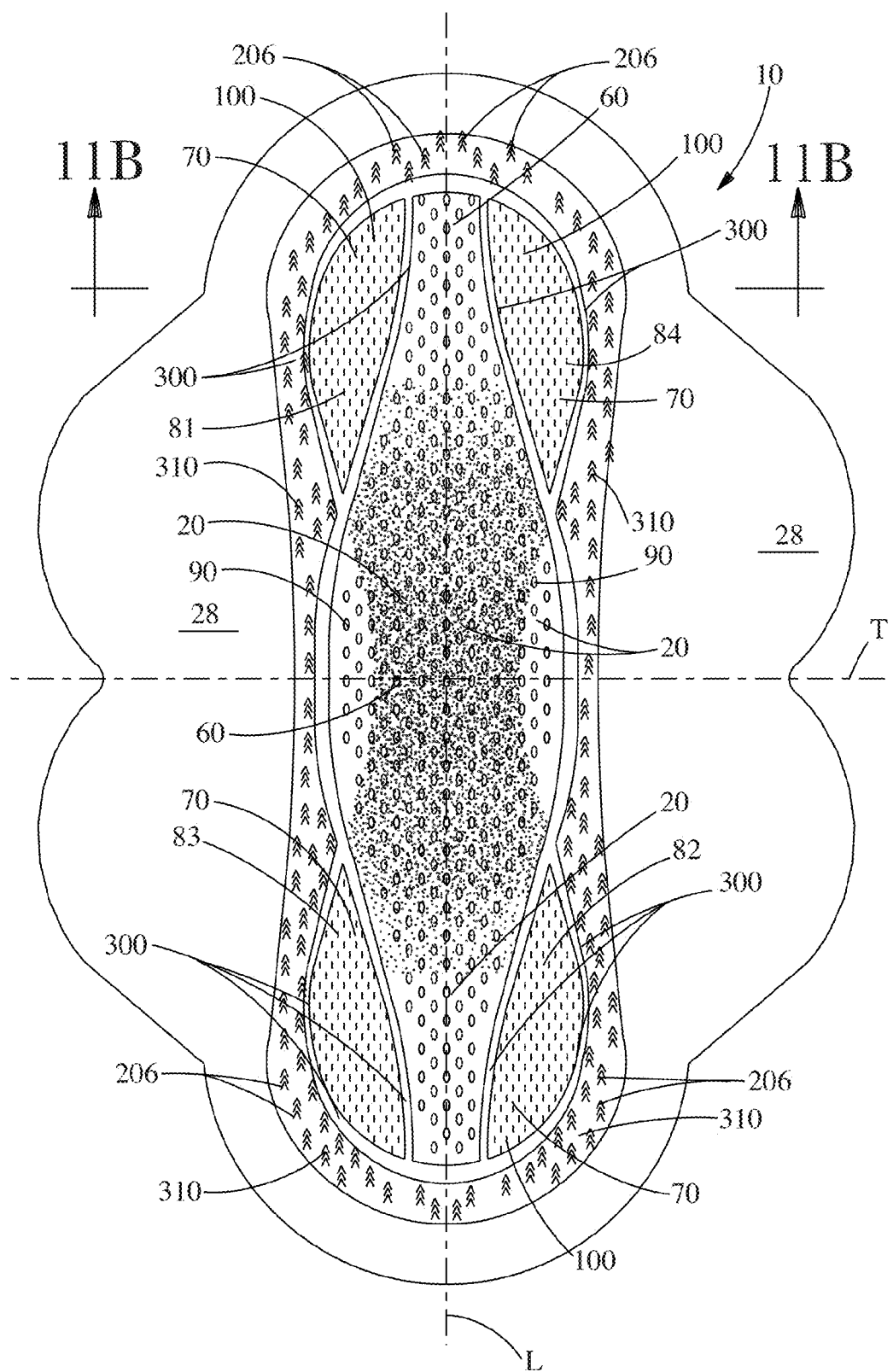
FIG. 11A is an illustration of an absorbent article having colored channels and a printed zone.
Figure 11B:
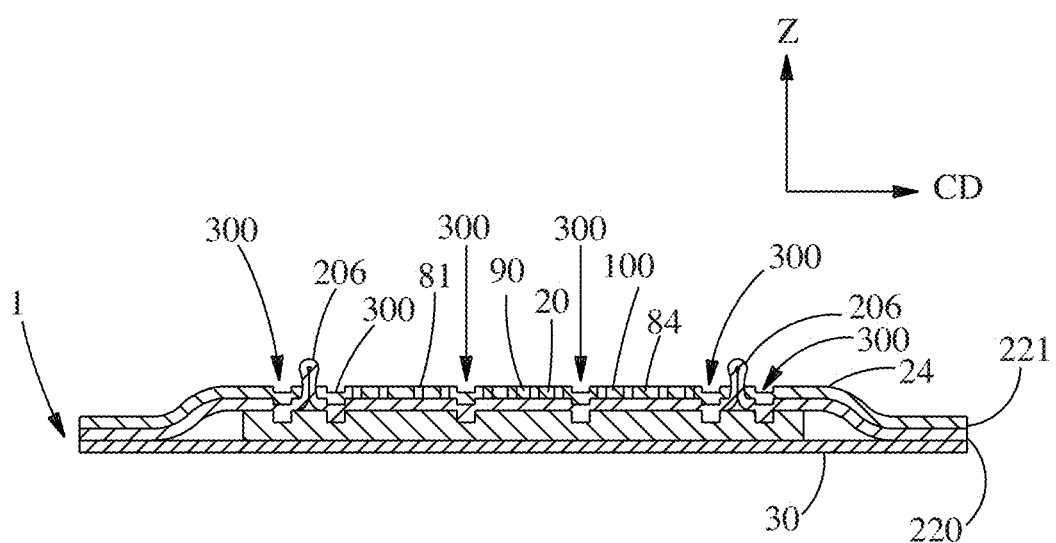
FIG. 11B a cross section as indicated by Section 11B in FIG. 11A.

In one embodiment, as shown in FIG. 11A the structurally modified zones can have a boundary wherein at least part of the boundary is defined by a channel 300. That is, for one or more of the structurally modified zones, a channel 300 can surround or partially surround the structurally modified zone and can be contiguous with that particular structurally modified zone. Channel 300 can be formed by any means known in the art for creating channels in absorbent articles. Suitable processes include compression molding in which the topsheet 20 and absorbent core 40 are compressed leaving an indentation in the body facing surface of the absorbent article. Without being bound by theory, it is thought that the capillary potential of the portion of the absorbent core 40 near a channel 300 can be higher than the capillary potential of portions of the absorbent core 40 away from the channel 300 and that the higher capillary potential can resist fluid transport beyond the channel 300. Similarly, the first portion 60 can also have a boundary wherein at least part of the boundary is defined by a channel 300.

In one embodiment, the topsheet 20 can comprise a third portion 310, as shown in FIG. 11A. The third portion 310 can at least partially bound or even completely bound both the first portion 60 and the second portion 70 in the plane defined by the longitudinal centerline and transverse centerline of the topsheet 20. The third portion 310 can be an apertured web having structures as disclosed above for the first portion 60 and second portion 70. The third portion 310 can comprise tufts 206, as shown in FIG. 11A. The third portion 310 can differ in structure from the first portion 60. The third portion 310 can differ in structure from the second portion 70. The third portion 310 can differ in structure from the first portion 60 and the second portion 70. The third portion 310 can differ in structure from a portions or portions selected from the group consisting of the first portion, the second portion, and both the first portion and second portion. Without being bound by theory, it is thought that by arranging a third portion 310 in this manner, the topsheet 20 can be provided with a peripheral structure that can be comforting to the wearer's skin and/or provide a barrier for flow of fluid on or near the surface of the absorbent article 10. In the context of a sanitary napkin worn in the crotch region, the third portion 310 at the front and back of the sanitary napkin can reduce the potential for leakage off of the sanitary napkin in these areas when the woman is lying on her back or front. The third portion 310 along the sides of the sanitary napkin can reduce the potential for lateral runoff from the sanitary napkin. The third portion 310 can comprise structures other than tufts 206.

In one embodiment, the third portion 310 can comprise tufts 206 of a soft nonwoven web. A third portion 310 comprising tufts 206 can provide for improved comfort of the absorbent article 10 when worn given that the peripheral edges of the absorbent article 10 may rub against the wearer's skin in her crotch area. The first portion 60 and/or second portion 70 of the topsheet 20 can be an apertured film having sufficient fluid acquisition characteristics and the third portion 310 can comprise tufts 206 formed of a nonwoven material to provide for comfort. This approach can provide for an absorbent article 10 that has adequate fluid acquisition properties near the center of the absorbent article 10 and can provide for comfort about the periphery of the absorbent article 10.

Absorbent core 40 can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers.

In one embodiment absorbent core 40 can be relatively thin, less than about 5 mm in thickness, or less than about 3 mm, or less than about 1 mm in thickness. Thickness can be determined by measuring the thickness at the midpoint along the longitudinal centerline of the pad by any means known in the art for doing while under a uniform pressure of 1.72 kPa. The absorbent core can comprise absorbent gelling materials (AGM), including AGM fibers, as is known in the art.

Backsheet 30 can comprise any of the materials known in the art for backsheets, such as polymer films and film/nonwoven laminates. To provide a degree of softness and vapor permeability for the garment-facing side of absorbent article 10, backsheet 30 can be a vapor permeable outer layer on the garment-facing side of the absorbent article 10. The backsheet 30 can be formed from any vapor permeable material known in the art. Backsheet 30 can comprise a microporous film, an apertured formed film, or other polymer film that is vapor permeable, or rendered to be vapor permeable, as is known in the art. One suitable material is a soft, smooth, compliant, vapor pervious material, such as a nonwoven web that is hydrophobic or rendered hydrophobic to be substantially liquid impermeable.

Other materials and components of absorbent articles 10 are contemplated to be within the scope of the description, including those disclosed in U.S. Pat. No. 4,950,264 issued to Osborn III Aug. 21, 1990 and U.S. Pat. No. 5,439,458 issued to Noel et al. Aug. 8, 1995.

Components of the absorbent article 10 can be joined by any means known in the art, such as by adhesive bonding, thermal bonding, ultrasonic bonding, and the like. An adhesive can be applied by means known in the art for laying a uniform layer of adhesive, such as by spraying or slot coating. The adhesive can be a fluid permeable adhesive, such as the aforementioned Findley HX1500-1 adhesive.

Fluid Handling Properties of Absorbent Article

The absorbent article of the present invention comprises fluid handling zones that are designed to customize the fluid handling properties of the absorbent article. The fluid handling zones of the present absorbent articles can correspond to the structurally modified zones of the absorbent article as described hereinbefore. Fluid handling zones can further correspond to channels in the absorbent article.

A fluid handling zone of the absorbent article of the present invention will exhibit a Transverse Fluid Travel Distance, a Longitudinal Fluid Travel Distance, an Acquisition Time, and a Rewet Value, each determined according to the test methods described hereinbelow.

In one embodiment, the absorbent article of the present invention comprises a first fluid handling zone comprising a first portion of a topsheet of the absorbent article and having a first Transverse Fluid Travel Distance, and a second fluid handling zone comprising a second portion of the topsheet and having a second Transverse Fluid Travel Distance. The first portion of the topsheet has a different construction than the second portion of said topsheet. The first Transverse Fluid Travel Distance is at least about 50% greater than said second Transverse Fluid Travel Distance.

In one embodiment, the first Transverse Fluid Travel Distance is at least 5 mm greater than the second Transverse Fluid Travel Distance.

In one embodiment, the absorbent article comprises a first fluid handling zone having a first Longitudinal Fluid Travel Distance and a second fluid handling zone having a second Longitudinal Fluid Travel Distance. The absorbent article further comprises a third fluid handling zone comprising a third portion of the topsheet and having a third Longitudinal Fluid Travel Distance. The third Longitudinal Fluid Travel Distance is greater than the first and second Longitudinal Fluid Travel Distances.

In one embodiment, the absorbent article further comprises a third fluid handling zone comprising a third portion of the topsheet having a different construction than the first and second portions of the topsheet, wherein the third fluid handling zone, preferably a channel, is disposed between the first and second fluid handling zones.

In one embodiment, the absorbent article comprises a first fluid handling zone having a first Acquisition Time, a second fluid handling zone having a second Acquisition Time, and a third fluid handling zone having a third Acquisition Time, wherein the third Acquisition Time is less, preferably at least about 50% less, than the first or second Acquisition Times.

In one embodiment, the absorbent article comprises a first fluid handing zone having a first Rewet Value and a second fluid handling zone having a second Rewet Value, wherein the first Rewet Value is less than the second Rewet Value.

In one embodiment, the absorbent article has a longitudinal centerline; wherein a first fluid handling zone intersects the longitudinal centerline and a second fluid handling zone does not intersect the longitudinal centerline.

In one embodiment, the absorbent article has a transverse centerline, wherein a first fluid handling zone and a second fluid handling zone both intersect the transverse centerline.

In one embodiment, the absorbent article has a transverse centerline, wherein a first fluid handling zone intersects the transverse centerline and a second fluid handling zone does not intersect the transverse centerline.

In one embodiment, the second fluid handling zone is present on opposing sides of the transverse centerline, wherein a width of the second fluid handling zone width is greater at locations on opposing sides of the transverse centerline than at the transverse centerline.

In one embodiment, the absorbent article comprises a first fluid handling zone disposed in the center of the absorbent article.

In one embodiment, the first fluid handling zone comprises an apertured film.

In one embodiment, the second fluid handling zone comprises a nonwoven web, preferably comprising tufts.

In one embodiment, the absorbent article comprises an absorbent core having a maximum absorbent core width orthogonal to a longitudinal centerline of the absorbent article, wherein the second fluid handling zone has a maximum second fluid handling zone width orthogonal to the longitudinal centerline, and wherein the maximum second fluid handling zone width is less than about 50%, preferably less than about 25%, of the maximum absorbent core width.

In one embodiment, the absorbent article is a sanitary napkin.

Figure 12:
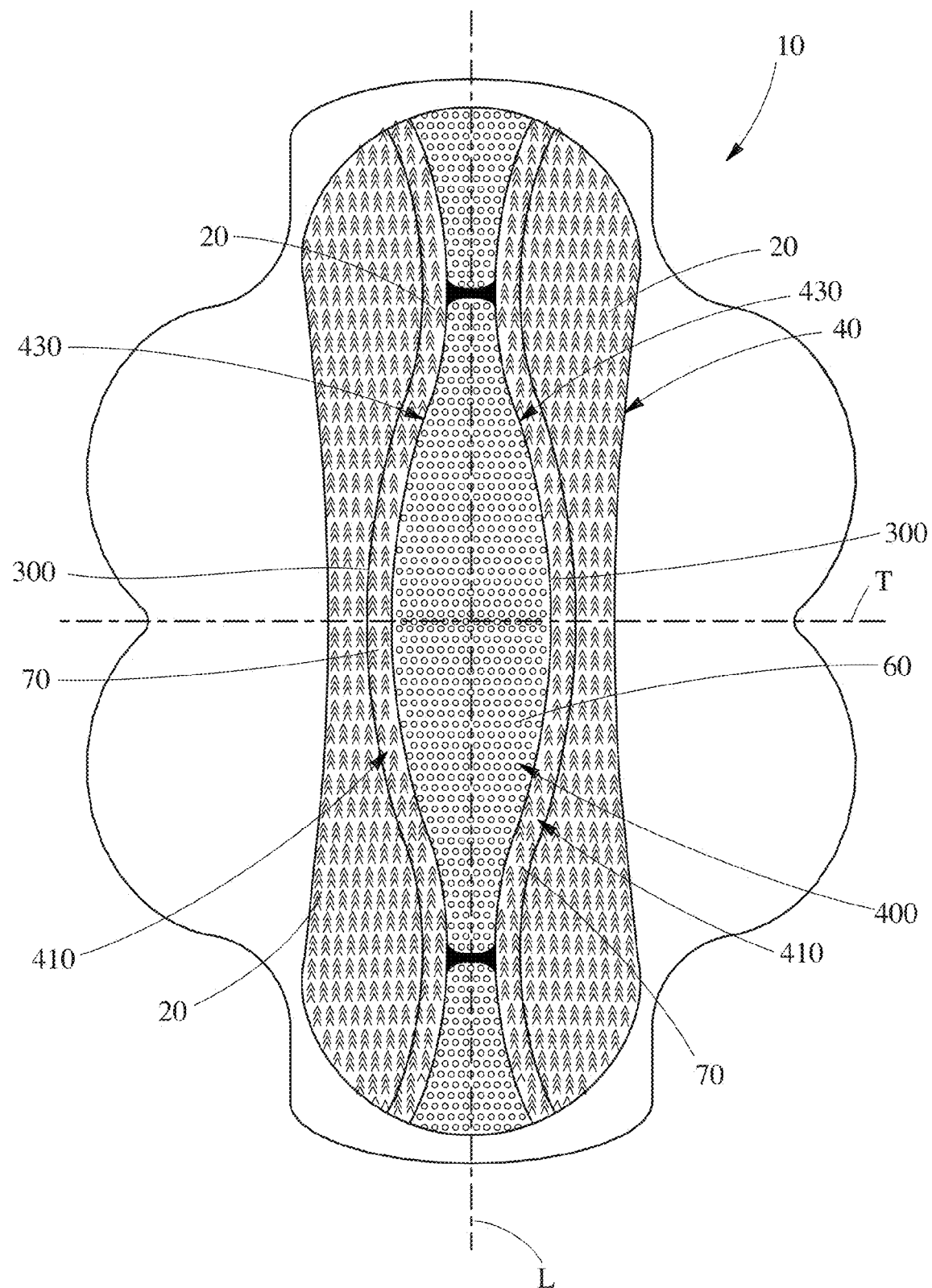
FIG. 12 is an illustration of an absorbent article comprising fluid handling zones.

FIG. 12 illustrates one embodiment of an absorbent article of the present invention comprising fluid handling zones. This embodiment is described in more detail in the Example hereinbelow.

TEST METHODS

The methods for assessing the fluid handling zones of the absorbent article of the present invention are as follows.

Artificial Menstrual Fluid Simulant ("AMFS")

The Artificial Menstrual Fluid Simulant (referred to herein as "AMFS") used in this testing is composed of 70% defibrinated sheep's blood and 30% of a solution comprised of melted gelatin, anionic polyacrylamide flocculant, and phosphate-buffered saline solution. Such an AMFS is described in more detail in U.S. Pat. No. 7,659,372.

The melted gelatin is prepared by combining 7 grams of edible-grade, unflavored gelatin with 85 grams of sterile distilled water. The components are heated and stirred until dissolution. The solution is allowed to solidify in a 4° C. refrigerator overnight. The phosphate-buffered saline solution is prepared by combining 22 grams of a solution containing 0.138% hydrous monobasic sodium phosphate and 0.85% sodium chloride with 70 grams of a solution containing 0.14% of anhydrous dibasic sodium phosphate and 0.85% sodium chloride. The anionic polyacrylamide flocculant, available from Kemira as Superfloc™ A-150, is prepared by combining 1 gram of the flocculant beads with a 1% sodium chloride solution in sterile distilled water. The solution is set at room temperature for one week.

To make 100 ml of AMFS, 7 grams of solidified gelatin is added to 21.5 grams phosphate-buffered saline solution and heated on a hotplate at 35° C. until visually melted. This solution is allowed to cool to 25° C. Then 1.5 grams of anionic polyacrylamide flocculant is added, followed by 70 grams of defibrinated sheep's blood available from Cleveland Scientific. The resulting AMFS is inverted ten times to ensure component mixing and is then placed in a 4° C. refrigerator overnight.

The AMFS viscosity is checked for testing suitability using a TA Instruments AR 1500 or AR 2000 rotational rheometer. After allowing the AMFS batch to warm to 25° C., it is tested at a 25° C. instrument temperature using a steel, 40 mm, 0° plate with a gap 500-1000 microns that ramps shear rate from 0.5 to 30 l/s. Linear regression is applied to the resulting shear curve and the viscosity is calculated for a shear rate of 20 l/s. An AMFS viscosity of 17-23 centipoise at 20 l/s is considered acceptable for use in the test methods herein.

Sample Preparation

Absorbent articles are unfolded and removed from all release papers/films/tapes. The absorbent article's adhesive is mitigated using a small film of cornstarch rubbed by hand to adhesive areas on the garment side and wings of the absorbent article. No more than 0.5 grams of cornstarch is necessary to achieve this.

Absorbent articles are allowed to incubate with their body-side surfaces exposed (ie. unfolded and its wings opened) for two hours prior to testing in a laboratory that has been climate-controlled for 73° F.+/−4, and 50% Rh+/−4.

For each fluid handling method described herein, the AMFS is applied to the absorbent articles using a 10 ml beaker. This facilitates rapid and continuous fluid delivery as well as protection from any viscosity shearing effects. Prior to testing, AMFS is loaded into a 10 ml beaker and then poured off. This measure sufficiently coats the interior of the beaker, allowing for accurate weights of fluid to be applied during testing. This is checked using a second loading where a 0.5 grams+/−0.05 of AMFS is added to the same beaker. This AMFS is poured over 2 seconds into a balance-torn weigh boat. The weight of this fluid should be 0.45-0.55 grams. This ensures accurate fluid application during testing.

Fluid Travel Distance Method

The absorbent article (with all release papers/films/tapes removed) is placed flat in either a longitudinal (i.e. machine direction or "MD") or transverse (i.e. cross-machine direction or "CD") orientation on a 30 cm×23 cm plexiglass plate that is set at a 15° incline relative to horizontal. AMFS is applied to the absorbent article in the fluid handling zone of interest and allowed to run down the surface of the absorbent article until complete absorption. If the absorbent article is placed in the longitudinal orientation on the plexiglass plate, 0.5 grams (+/−0.05 grams) of AMFS is used for the test. If the absorbent article is placed in the transverse orientation on the plexiglass plate, 0.25 grams (+/−0.05 grams) of AMFS is used for the test. These volumes ensure complete fluid absorption within the particular fluid handling zone of interest without any substantial intrusion into adjacent fluid handling zones on the absorbent article. Using a 10 ml beaker, AMFS is applied by pouring the orientation-dependent volume for two seconds into the fluid handling zone of interest at a point that is a minimum of 5 mm inboard of the upmost edge of the fluid handling zone of interest. Using a ruler capable of measuring to 1 mm, the distance the AMFS traveled is measured lengthwise to the longitudinal axis of the absorbent article when the absorbent articles is place in the longitudinal orientation on the plexiglass plate and widthwise to the longitudinal axis of the absorbent article when the absorbent article is place in the transverse orientation on the plexiglass plate. Measurements are made to the nearest millimeter from the point of application of AMFS onto the surface of the absorbent article to the terminal point where complete AMFS absorption occurs. If this measurement is made when the absorbent article is placed in the longitudinal orientation on the plexiglass plate, the distance measured is reported as the "Longitudinal Fluid Travel Distance" or "MD Fluid Travel Distance". If this measurement is made when the absorbent article is placed in the traverse orientation on the plexiglass plate, the distance measured is reported as the "Transverse Fluid Travel Distance" or "CD Fluid Travel Distance".

Fluid Acquisition Time Method

The absorbent article (with all release papers/films/tapes removed) is placed flat on a light box top (e.g. The Back Light Series, Model #BL1012, 13 watt bulb available from Hall Productions), which is used to illuminate through the article. The light box is able to illuminate through both thin cellulose air-laid based, as well as thick fluff-pulp based, absorbent articles. A 50.98 gram stainless steel cylinder that is 0.995 inches long, has a 0.745 square inch base, and a 0.208 inch diameter aperture that remains open through the entire central axis, is placed so that its base rests flat upon the absorbent article in the fluid handling zone of interest. The cylinder will impart 0.25 psi to the fluid handling zone of the absorbent article directly beneath it. Using a 10 ml beaker, 0.5 gram AMFS+/−0.05 is rapidly applied to the absorbent article through the aperture top. A stopwatch capable of measuring to 0.1 seconds is simultaneously initiated the moment the poured fluid enters the top of the aperture of the stainless steel cylinder. The absorbent article is visually monitored directly from above through the top of the aperture of the stainless steel cylinder. The stopwatch time is terminated the moment the surface of the absorbent article is visible through the aperture of the stainless steel cylinder. This determination is enabled by the light box which illuminates the surface of the absorbent article once the AMFS has been absorbed. The time recorded by the stopwatch is reported as the "Acquisition Time" for the particular fluid handling zone of interest.

Fluid Rewet Method

The absorbent article (with all release papers/films/tapes removed) is placed flat in either a longitudinal (i.e. machine direction or "MD") or transverse (i.e. cross-machine direction or "CD") orientation on a 30 cm×23 cm plexiglass plate that is set at a 15° incline relative to horizontal. Doses of AMFS are applied to the absorbent article and allowed to run down its surface until complete absorption. In the longitudinal orientation, 1.0 gram of AMFS+/−0.05 grams is used and in the transverse orientation, 0.5 grams AMFS+/−0.05 grams is used. These volumes ensure complete fluid absorption within the single fluid handling zone of interest without any substantial intrusion into adjacent fluid handling zones on the absorbent article. Using a 10 ml beaker, AMFS is applied by pouring the orientation-dependent volume over two seconds into each fluid handling zone of interest at a point that is a minimum of 5 mm inboard of the upmost edge of the fluid handling zone of interest. For the fluid handling zone comprising a channel, AMFS is applied to any point in the channel that is greater than 10 cm from the channel's terminus in the longitudinal orientation. In the transverse orientation, AMFS is applied at any point in the channel. One minute after the AMFS application, a stack of seven, 5 inch by 5 inch, Model #632 Ahlstrom filter papers each having a basis weight of 0.093 g/in$^2$ that have been torn to zero on an analytical balance are placed upon the and centered upon the resulting stain on the absorbent article while still on the incline. An in-house constructed, 1179 gram, 8 inch lengthwise by 3 inch widthwise, 1.5 inch thick weight composed both of steel and 1 inch thick polyurethane foam having a 0.57 psi firmness, a 9 psi tensile strength and a density of 2.8 lbs./ft$^3$ and wrapped in 0.04 mm thick, polyethylene is placed, foam side down upon the filter paper stack for 5 seconds and then removed. The stack of filter papers are removed and weighed on an analytical balance capable of measuring to the nearest 0.01 gram. The weight of any collected fluid on the filter papers is the re-wet weight and recorded as the "Rewet Value".

EXAMPLE

FIG. 12 illustrates an example of an absorbent article 10 of the present invention comprising a topsheet 20, a secondary topsheet underlying the topsheet, an absorbent core 40 underlying the secondary topsheet, and a liquid impervious backsheet underlying the absorbent core. The topsheet 20 comprises a laminate of 100 mesh microapertured and macroapertured polyethylene film (available from Tredegar Film Products) and a 28 gsm spunbond nonwoven comprising polyethylene/polypropylene bicomponent fibers (available from BBA Nonwovens). The secondary topsheet underlying the topsheet 20 is a 95 gsm airlaid fibrous web (available from Rexell). The absorbent core 40 underlying the secondary topsheet is a 195 gsm airlaid absorbent core (available from Concert). The liquid impervious backsheet underlying the absorbent core is a liquid impervious polyethylene film.

The absorbent article 10 comprises a first fluid handling zone 400 comprising first portion 60 of a topsheet 20. The absorbent article further comprises a second fluid handling zone 410 comprising a second portion 70 of the topsheet 20. The first portion 60 of the topsheet 20 comprises a polyethylene film comprising macroapertures and microapertures. The second portion 70 of the topsheet 20 comprises a structurally modified zone 81 comprising tufts 206. The tufts are described in detail in U.S. application Ser. No. 12/415,140 filed Mar. 31, 2009. The first fluid handling zone 400 and the second fluid handling zone 410 are separated by a third fluid handling zone 430 comprising a channel 300 that has a width ranging from about 1.5 mm to about 4.2 mm.

This absorbent article is tested according to the Fluid Travel Distance Method, the Fluid Acquisition Time Method, and the Fluid Rewet Method. The results of the testing are shown in the following table:

| Topsheet Fluid Handling Zone | CD Fluid Travel Distance (cm) | MD Fluid Travel Distance (cm) | Acquisition Time (sec) | CD Rewet Value (g) | MD Rewet Value (g) |
| --- | --- | --- | --- | --- | --- |
| First Zone | 1.5 ± 0.2 | 3.5 ± 0.5 | 14.3 ± 3.6 | 0.01 ± 0.01 | 0.02 ± 0 |
| Second Zone | 0.9 ± 0.4 | 2.7 ± 0.5 | 12.5 ± 3.4 | 0.04 ± 0.01 | 0.10 ± 0.04 |
| Third Zone | 0.9 ± 0.4 | 6.0 ± 0.8 | 3.8 ± 1.5 | 0.02 ± 0 | 0.03 ± 0 |

COMPARATIVE EXAMPLE

A commercially available product, ALWAYS DRI-LINERS Regular Unscented, is tested according to the Fluid Travel Distance Method as a comparative example. The ALWAYS DRI-LINERS Regular Unscented product comprises a topsheet having a portion comprised of a nonwoven/film laminate material and a second portion comprised of a film material. The results of the test are shown in the following table:

| Topsheet Portion | CD Fluid Travel Distance (cm) | MD Fluid Travel Distance (cm) |
| --- | --- | --- |
| Film Material | 1.7 ± 0.5 | 8.3 |
| Nonwoven/Film Laminate Material | >1.8 | 15.0 |

This data illustrates that the film material portion of the topsheet exhibits a lower CD Travel Distance value than the nonwoven/film laminate material portion of the topsheet.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An absorbent article comprising:
    a topsheet;
    a backsheet;
    an absorbent core disposed between said topsheet and said backsheet;
    a longitudinal centerline;
    a transverse centerline;
    a first fluid handling zone comprising a first portion of said topsheet and having a first Transverse Fluid Travel Distance, wherein said first portion comprises a structurally modified zone that does not include a channel, indentation, dimple or embossment;
    a second fluid handling zone comprising a second portion of said topsheet and having a second Transverse Fluid Travel Distance, wherein said second portion comprises a structurally modified zone that does not include a channel, indentation, dimple or embossment; and
    a third fluid handling zone comprising a third portion of said topsheet, wherein said third portion comprises a structurally modified zone that does not include a channel, indentation, dimple or embossment, wherein said third portion of said topsheet is on opposite sides of both said transverse centerline and said longitudinal centerline than that of said second portion of said topsheet;
    wherein said first portion of said topsheet has a different construction than said second portion of said topsheet;
    wherein said second portion of said topsheet has a different construction than said third portion of said topsheet; and
    wherein said first Transverse Fluid Travel Distance is at least 50% greater than said second Transverse Fluid Travel Distance.

2. The absorbent article of claim 1, wherein said first fluid handling zone has a first Rewet Value and said second fluid handling zone has a second Rewet Value; wherein said first Rewet Value is less than said second Rewet Value.

3. The absorbent article of claim 1, wherein said first fluid handling zone intersects said longitudinal centerline and said second fluid handling zone does not intersect said longitudinal centerline.

4. The absorbent article of claim 1, wherein said first fluid handling zone intersects said transverse centerline and said second fluid handling zone does not intersect said transverse centerline.

5. The absorbent article of claim 1, wherein said first fluid handling zone is disposed in the center of said absorbent article.

6. The absorbent article of claim 1, wherein said first Transverse Fluid Travel Distance is at least 5 mm greater than said second Transverse Fluid Travel Distance.

7. The absorbent article according to claim 1, wherein said first fluid handling zone comprises an apertured film.

8. The absorbent article according to claim 1, wherein said second fluid handling zone comprises a nonwoven web.

9. The absorbent article of claim 1, wherein said absorbent core has a maximum absorbent core width orthogonal to a longitudinal centerline of said absorbent article, wherein said second fluid handling zone has a maximum second fluid handling zone width orthogonal to said longitudinal centerline, and wherein said maximum second fluid handling zone width is less than 50% of said maximum absorbent core width.

10. The absorbent article according to claim 9, wherein said maximum second fluid handling zone width is less than 25% of said maximum absorbent core width.

11. The absorbent article of claim 1, wherein said absorbent article is a sanitary napkin.

12. The absorbent article according to claim 1, wherein the topsheet comprises two layers of nonwoven.

13. The absorbent article according to claim 1, wherein the topsheet comprises both a film layer and a nonwoven layer.

14. An absorbent article comprising:
    a topsheet;
    a backsheet;
    an absorbent core disposed between said topsheet and said backsheet;
    a longitudinal centerline;
    a transverse centerline;
    a first fluid handling zone comprising a first portion of said topsheet and having a first Transverse Fluid Travel Distance, wherein said first portion comprises a structurally modified zone that does not include a channel, indentation, dimple or embossment; and
    a second fluid handling zone comprising a second portion of said topsheet and having a second Transverse Fluid Travel Distance, wherein said second portion comprises a structurally modified zone that does not include a channel, indentation, dimple or embossment;
    wherein said second fluid handling zone does not intersect said longitudinal centerline;
    wherein said second fluid handling zone does not intersect said transverse centerline;
    wherein said first portion of said topsheet has a different construction than said second portion of said topsheet; and
    wherein said first Transverse Fluid Travel Distance is at least 50% greater than said second Transverse Fluid Travel Distance.

15. The absorbent article according to claim 14, wherein said second portion is proximate a transverse end of said absorbent article but does not extend all the way to said transverse end.

16. An absorbent article comprising:
    a topsheet;
    a backsheet;
    an absorbent core disposed between said topsheet and said backsheet;

a longitudinal centerline;
a transverse centerline;
a first fluid handling zone comprising a first portion of said topsheet comprising a structurally modified zone that does not include a channel, indentation, dimple or embossment;
a second fluid handling zone comprising a second portion of said topsheet comprising a structurally modified zone that does not include a channel, indentation, dimple or embossment; and
a third fluid handling zone comprising a third portion of said topsheet comprising a structurally modified zone that does not include a channel, indentation, dimple or embossment, wherein said third portion of said topsheet is on opposite sides of both said transverse centerline and said longitudinal centerline than that of said second portion of said topsheet;
wherein said first portion of said topsheet has a different construction than said second portion of said topsheet; and
wherein said second portion of said topsheet has a different construction than said third portion of said topsheet.

* * * * *